(12) United States Patent
Landesberg et al.

(10) Patent No.: US 11,638,534 B2
(45) Date of Patent: May 2, 2023

(54) CONTINUOUS MONITORING OF THE PERFUSION OF AN ORGAN OR EXTREMITY

(71) Applicants: TECHNION RESEARCH, Haifa (IL); THE MEDICAL RESEARCH INFRASTRUCTURE AND HEALTH SERVICES FUND OF THE TEL AVIV MEDICAL CENTER, Tel Aviv (IL)

(72) Inventors: Amir Landesberg, Haifa (IL); Amit Livneh, Hofit (IL); Yehuda Wolf, Mevaseret Zion (IL)

(73) Assignee: The Medical Research Infrastructure and Health Services Fund of the Tel Aviv Medical Center, Tel Aviv (IL)

( * ) Notice: Subject to any disclaimer, the term of this patent is extended or adjusted under 35 U.S.C. 154(b) by 53 days.

(21) Appl. No.: 16/626,590

(22) PCT Filed: Jun. 26, 2018

(86) PCT No.: PCT/IB2018/054703
§ 371 (c)(1),
(2) Date: Dec. 26, 2019

(87) PCT Pub. No.: WO2019/003105
PCT Pub. Date: Jan. 3, 2019

(65) Prior Publication Data
US 2020/0121200 A1    Apr. 23, 2020

Related U.S. Application Data

(60) Provisional application No. 62/524,719, filed on Jun. 26, 2017.

(51) Int. Cl.
*A61B 5/0295* (2006.01)
*A61B 5/0205* (2006.01)
(Continued)

(52) U.S. Cl.
CPC ............ *A61B 5/0295* (2013.01); *A61B 5/022* (2013.01); *A61B 5/0205* (2013.01);
(Continued)

(58) Field of Classification Search
CPC ..... A61B 5/0295; A61B 5/352; A61B 5/0205; A61B 5/022; A61B 5/0535;
(Continued)

(56) References Cited

U.S. PATENT DOCUMENTS

2003/0167012 A1* 9/2003 Friedman ........... A61B 5/02125
600/506
2009/0043179 A1    2/2009 Melker
(Continued)

FOREIGN PATENT DOCUMENTS

WO    2016/040263    3/2016

OTHER PUBLICATIONS

Fales JT, Heisey, SR, Zierler KL. Blood flow from and oxygen uptake by muscle, during and after partial venous occlusion. American Journal of Physiology. Sep. 1962;203(3):470-474. (Year: 1962).*
(Continued)

*Primary Examiner* — Mallika D Fairchild
*Assistant Examiner* — Shreya Anjaria
(74) *Attorney, Agent, or Firm* — Dekel Patent Ltd.; David Klein

(57) ABSTRACT

A method and system are provided for continuous monitoring perfusion of an organ or extremity, and for early detection of progressive partial occlusion of arterial blood supply or venous drainage of tissue. The method and system measure a delay in wave propagation of a blood perfusion wave, which is associated with flow of blood through a blood vessel. The delay is correlated to an amount of obstruction in the blood vessel.

15 Claims, 21 Drawing Sheets

(51) Int. Cl.
*A61B 5/022* (2006.01)
*A61B 5/0535* (2021.01)
*A61B 5/352* (2021.01)
*A61B 5/1455* (2006.01)
*A61B 5/00* (2006.01)

(52) U.S. Cl.
CPC ............ *A61B 5/0535* (2013.01); *A61B 5/352* (2021.01); *A61B 5/14551* (2013.01); *A61B 5/7203* (2013.01); *A61B 2562/0219* (2013.01)

(58) Field of Classification Search
CPC . A61B 5/14551; A61B 5/7203; A61B 5/0803; A61B 5/318; A61B 5/021; A61B 5/726; A61B 2562/0219
See application file for complete search history.

(56) References Cited

U.S. PATENT DOCUMENTS

| | | | |
|---|---|---|---|
| 2010/0016694 A1 | 1/2010 | Martin | |
| 2010/0016696 A1* | 1/2010 | Addison | A61B 5/726 |
| | | | 382/128 |
| 2015/0065827 A1* | 3/2015 | Frederick | A61B 5/7282 |
| | | | 600/324 |
| 2016/0287172 A1* | 10/2016 | Morris | A61B 5/7264 |
| 2017/0281024 A1* | 10/2017 | Narasimhan | A61B 5/681 |

OTHER PUBLICATIONS

Allen J. et al. A prospective comparison of bilateral photoplethysmography versus the ankle-brachial pressure index for detecting and quantifying lower limb peripheral arterial disease. Journal of Vascular Surgery. Apr. 2008;47(4):794-802. doi: 10.1016/j.jvs.2007.11.057 (Year: 2008).*

Allen J, Oates CP, Lees TA, Murray A. Photoplethysmography detection of lower limb peripheral arterial occlusive disease: a comparison of pulse timing, amplitude and shape characteristics. Physiol Meas. Oct. 2005;26(5):811-21. doi: 10.1088/0967-3334/26/5/018. Epub Jul. 6, 2005. PMID: 16088070. (Year: 2005).*

PCT Search Report and Written Opinion PCT/IB2018/054703, dated Nov. 6, 2018.

"Photoplethysmography detection of lower limb peripheral arterial occlusive disease: a comparison of pulse timing, amplitude and shape characteristics", Physiological Measurement, vol. 26, No. 5, pp. 811-821, Jul. 6, 2005.

* cited by examiner

| Index Name | Baseline 45 (mmHg) | Occlusion 45 (mmHg) | Occlusion 90 (mmHg) | p 45vs Baseline | p90 vs BL | p90 vs.45 |
|---|---|---|---|---|---|---|
| Peak Perfusion Delay (s) | 0.364 ± 0.005 | 0.414 ± 0.020 | 0.444 ± 0.012 | 0.000 | 0.000 | 0.001 |
| Slow perfusion phase duration | 0.074± 0.016 | 0.176± 0.077 | 0.171± 0.044 | 0.006 | 0.000 | 0.877 |
| Slow-Rise Inflow Filling (%) | 16.4 ± 6.9 | 23.9 ± 7.2 | 29.5 ± 10.9 | 0.008 | 0.014 | 0.140 |
| Pulse Transit Time (s) | 0.167 ± 0.012 | 0.108 ± 0.084 | 0.155 ± 0.041 | 0.093 | 0.428 | 0.263 |
| Crest Time (s) | 0.198 ± 0.014 | 0.306 ± 0.075 | 0.289 ± 0.040 | 0.005 | 0.000 | 0.643 |
| Crest Width (s) | 0.057 ± 0.008 | 0.067 ± 0.008 | 0.059 ± 0.008 | 0.010 | 0.751 | 0.108 |
| Pulse Amplitude (Ohm) | 0.114 ± 0.024 | 0.118 ± 0.029 | 0.102 ± 0.023 | 0.571 | 0.035 | 0.075 |
| ABI | 1.21 ± 0.103 | 1.22± 0.17 | 1.18 ± 0.184 | 0.445 | 0.578 | 0.265 |
| O$_2$ Saturation (%) | 97.036 ± 0.744 | 97.160 ± 0.626 | 96.914 ± 1.335 | 0.593 | 0.687 | 0.598 |

FIG. 10H

TABLE 1

CONTINUOUS MONITORING OF THE PERFUSION OF AN ORGAN OR EXTREMITY

FIELD OF THE INVENTION

The invention relates to the field of continuous monitoring of an organ or extremity and early detection of progressive regional and partial occlusion of the arterial blood supply or venous drainage.

BACKGROUND

Peripheral artery disease (PAD) is a common problem that affects many of the elderly population. In the United States, over 6.8 million people over the age of forty have suffered from PAD. In 2010, in the United States, 146,000 patients were discharged from hospitals from PAD related treatments.

PAD is characterized by chronic and gradual progression. It is associated with chronic leg pain, fatigue, intermittent claudication, and necrosis of the distal parts that leads to leg amputation. Early diagnosis and treatment may allow appropriate interventions, at early stages, which will improve the quality of life and will prevent amputation. Venous diseases, such as deep vein thrombosis, may cause severe pain and lead to pulmonary emboli and/or death.

Current clinical diagnosis is based primarily on flow measurement by ultrasound Doppler, and assessment of differences in blood pressures between legs and arms of a patient, e.g. Ankle Brachial Index (ABI).

Several systems attempt to diagnose PAD, by using more detailed measurements for quantification of the peripheral hemodynamics. Some systems determine the ABI by simultaneous measurement of the blood pressure on arms and ankles (ABI), using four cuffs (Mesi-Medical: http://www.mesimedical.com). Some other systems perform pulse-oscillometry measurements, utilizing photo-plethysmography (PPG) on fingers and toes or impedance plethysmography (IPG) on arms and legs (Medis systems: https://medis.company/cms/index.php?page=products), with or without electrocardiogram (ECG) measurements. Some systems measure also the IPG after complete occlusion—to assess the reactive hyperemic response.

These pulse-oscillometry measurements are usually used to derive four parameters: crest time (CrT, ms)—the period from the onset of an increase in the slope of the IPG to the maximum point of the curve; crest width (CW, ms)—the time between two points of the plethysmographic curve around the maximum, at 95% of the maximum; pulse amplitude (Pampl, $\Omega$); and, Alternative Blood Flow (ABF, %/min)—to quantify changes in the volume during the cardiac cycle, based on the amplitude, CrT and the duration of the systole.

These clinical diagnostic modalities have significant disadvantages: they are done sporadically (as opposed to the need for continuous monitoring), and they require professional skills. Doppler measurements depend on the availability of professional technicians and physicians. The patients usually repeat the examination every 4-6 months.

The ABI tests have low sensitivity and predictive values and result in high false negative rates. According to the American Heart Association (AHA), using these modalities can result in a significant portion of patients diagnosed in a late stage of disease with lower extremity ulcers and angiographically proven severe disease.

The foregoing examples of the related art and limitations related therewith are intended to be illustrative and not exclusive. Other limitations of the related art will become apparent to those of skill in the art upon a reading of the specification and a study of the figures.

SUMMARY

The following embodiments and aspects thereof are described and illustrated in conjunction with systems, tools and methods which are meant to be exemplary and illustrative, not limiting in scope.

In one aspect, the measurement of the wave propagation associated with blood perfusion (arterial or venous delivery of blood) is used to measure occlusions in blood lumens.

The prior art has not considered measurement of the wave propagation associated with blood perfusion to be a valid technique for measuring peripheral artery disease because it is assumed that hardening of arterial walls will accelerate wave propagation associated with blood perfusion. Surprisingly, the inventors have found the opposite is true: the anatomy of the blood vessels with peripheral artery disease or with arterial lesions actually causes delays in the wave propagation. The amount of delay in the wave propagation associated with blood perfusion is directly correlated to the amount of peripheral artery disease or arterial lesions. Furthermore, the invention differentiates between the respiratory and cardiac modulations of the perfusion waves, which differentiates between the presence of arterial lesions as opposed to venous lesions: partial arterial occlusion attenuates the cardiac component of the monitored perfusion waves whereas partial venous occlusion attenuates the respiratory component of the monitored perfusion waves.

There is provided, in accordance with an embodiment, a method comprising using at least one hardware processor for receiving measurements of vital signs from a plurality of sensors; performing a wavelet coherence analysis; obtaining reference events; determining the fiducial points for alignment and analysis of large number of heart cycles; generating a median event interval; calculating a representative signal complex out of acquired large number of heart cycle; performing a segmentation; and, extracting features.

In some embodiments, the method further comprises performing a baseline wonder removal and noise removal; performing decimation to reduce computation time, power consumption, memory consumption and data transfer loads; and, matching filter application of the representative signal complex in order to improve event detection rates.

In some embodiments, performance of the wavelet coherence analysis jointly tests a temporal and frequency attributes of blood volume in a leg of the subject through impedance signals.

In some embodiments, the extracted feature enables estimating the adaptive response of the microcirculation to changes in the patency of the artery that supply the periphery changes in the venous drainage, based on changes in the time and frequency attributes.

In some embodiments, progressive partial occlusion is manifested by reduction of an energy magnitude of higher frequencies of arterial frequency band.

In some embodiments, the set of windows are registered proportionally to a period signal used to determine the heart rate and to define fiducial points, wherein the periodic signal is an ECG.

In some embodiments, the periodic signal is a pulse oximetry point.

There is provided, in accordance with an embodiment, a detection system, comprising a plurality of sensors obtaining measurements of vital signs of a subject, and at least one hardware processor configured to: receiving measurements of vital signs from a plurality of sensors; performing a wavelet coherence analysis; obtaining reference events; determining the fiducial points for alignment and analysis of large number of heart cycles; generating a median event interval; calculating a representative signal complex out of acquired large number of heart cycle; estimating heart rate variability; performing a segmentation; and, extracting features.

In some embodiments, the plurality of sensors comprises ECG electrodes placed on the arms or chest of the subject a reference electrode is placed on the abdomen of the subject; a pulse oximeter probe attached to a finger of the subject; a respiration-monitoring belt placed on the chest to measure respiration of the subject; a impedance plethysmography on one or more extremities; and an photoplethysmogram on one or more extremities.

In some embodiments, the extracted features comprise change in the delay of the perfusion filling wave arrival; symmetrical delay in the perfusion filling wave arrival; changes in the shape of the perfusion wave, with slowing of the downslope; significant changes in the power spectrum of the perfusion wave, with attenuation of the higher frequencies; changes in the respiratory and cardiac bands in the power spectrum; changes in the coherence of the waves between the extremities, each one against the contralateral or the three others; and, changes over time in the over indices compromising: time delays, downslope rates, high frequency band of the arterial contents, cardiac versus breath bands and coherence between extremities.

There is provided in accordance with an embodiment of the invention a method for assessing obstruction in a blood vessel including measuring a delay in wave propagation of a blood perfusion wave, which is associated with flow of blood through a blood vessel, and correlating the delay to an amount of occlusion in the blood vessel, wherein if the delay is greater, the amount of occlusion is greater.

In another aspect the method includes measuring a wave propagation of a blood perfusion wave, which is associated with flow of blood through a blood vessel, and differentiating between respiratory and cardiac modulations of the perfusion wave, wherein attenuation of a cardiac component of the perfusion wave indicates partial arterial occlusion, and attenuation of a respiratory component of the perfusion wave indicates partial venous occlusion.

There is provided in accordance with an embodiment of the invention a system for assessing obstruction in a blood vessel including a sensor configured to measure a delay in wave propagation of a blood perfusion wave, which is associated with flow of blood through a blood vessel, and a processor configured to correlate the delay to an amount of occlusion in the blood vessel, wherein if the delay is greater, the amount of occlusion is greater.

BRIEF DESCRIPTION OF THE FIGURES

Exemplary embodiments are illustrated in referenced figures. Dimensions of components and features shown in the figures are generally chosen for convenience and clarity of presentation and are not necessarily shown to scale. The figures are listed below.

FIG. 10H (Table 1) is a statistical summary of the indices which were derived from the time domain analysis of impedance and photo plethysmography signals, in accordance with an embodiment of the invention;

DETAILED DESCRIPTION

Figure 1:
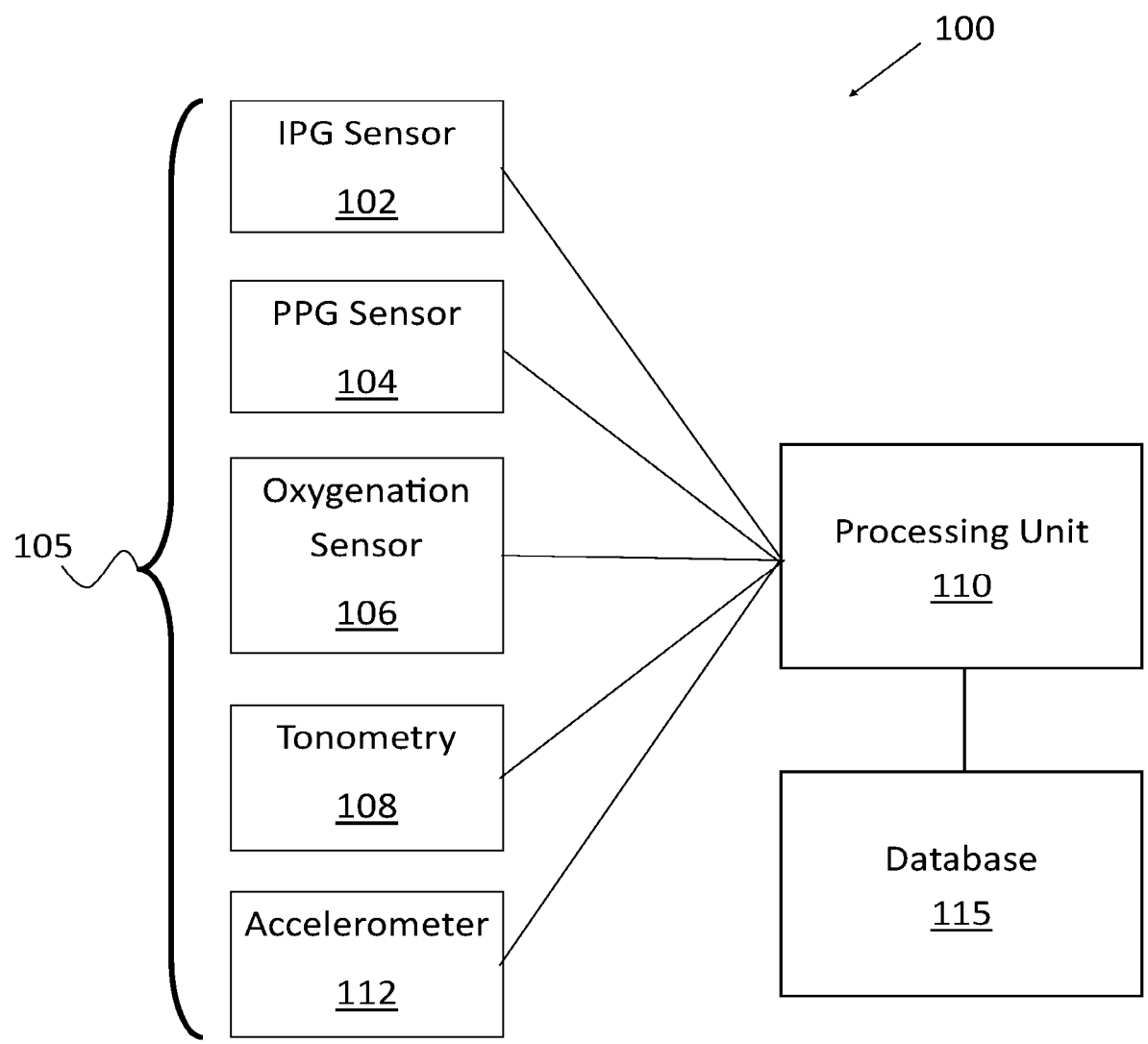
FIG. 1 shows a detection system to continuously monitor blood perfusion to lower extremities, according to certain embodiments.

Disclosed herein is a system and method for continuous monitoring of an organ or extremity by utilizing a set of non-invasive miniaturized sensors, and calculating indices of the perfusion dynamics. An adequate peripheral perfusion requires normal blood supply by the arteries and patent venous system. The novel suggested technology relates to both the arterial and venous systems.

The invention employs measurement of blood perfusion but is not limited to any particular measurement method. Both invasive and non-invasive methods are used to measure blood perfusion. One invasive method introduces microspheres in the blood vessels. Another invasive method uses implanted temperature sensors. Non-invasive methods include magnetic resonance imaging (MRI) (which may use injection of a tracer in the blood, arterial spin labeling and other techniques), positron emission tomography (PET) with a radioactive tracer introduced into the blood, thermal diffusion probe (TDP), laser Doppler flow meter (LDF), optical measurement techniques and others.

Progressive partial occlusion of a large artery yields pathognomonic changes in the perfusion dynamics, and may be measured and quantified in a time-frequency domain. These pathognomonic changes may be simply, non-invasively, and continuously monitored to improve precise diagnosis and detection of partial obstruction before it becomes symptomatic and causes irreversible damage. The system and method herein may apply to any organ. The system and method are exemplified herein via certain non-limiting embodiments of monitoring a perfusion of a lower extremity, and on quantification of a severity of Peripheral Artery Disease (PAD). Deterioration of PAD affects the arterial pressure as measured via an Ankle Brachial Index (ABI), the peak flow in a large artery and dynamics of tissue perfusion.

A detection system may be configured to monitor dynamics of tissue perfusion, for example by analyzing changes in waveforms acquired by the detection system. The detection system may comprise a plurality of sensors configured to measure vital signs related to the dynamics of the tissue perfusion. The plurality of sensors may comprise a sensor to measure a waveform of impedance plethysmography (IPG), a sensor to measure a waveform of photoplethysmogrphy (PPG), a sensor to measure a waveform of tissue oxygenation (Pulse oximetry), a sensor to monitor tonometry, accelerometers, and/or the like. The PPG sensor may enable monitoring volumetric changes in blood vessels diameters in the dermis and subcutaneous tissue. The tonometry may characterize a pressure wave and its relation to the perfusion wave. The accelerometers may determine changes in the position and patient's movements, which may be used in the analysis and to remove artifacts.

In certain embodiments, the plurality of sensors may be configured in wearable socks, isolated strips, belts, flexible rings, and/or the like. The plurality of sensors may transmit the measurement to nearby acquisition and analysis components, e.g. a processing unit of the detection system. The analyses and the decision making may be based on telemedicine principles.

FIG. 1 shows a detection system to continuously monitor blood perfusion to lower extremities, according to certain embodiments. Detection system 100 may comprise a plurality of sensors 105 which may be configured to measure vital signs of a subject. Plurality of sensors 105 may include an IPG sensor 102 to measure the waveform of IPG, a PPG sensor 104 to measure the waveform of PPG, an oxygenation sensor 106 to measure the waveform of tissue oxygenation, a tonometry sensor 108 to monitor tonometry, accelerometers 112, and/or the like. Detection system 100 may comprise a processing unit 110, which may be configured to analyze the measurements received from plurality of sensors 105. Detection system 100 may comprise a database, which may be configured to store patient information and comparison data. Similar sensors, as IPG or PPG may be placed on either legs or hands.

Figure 2:
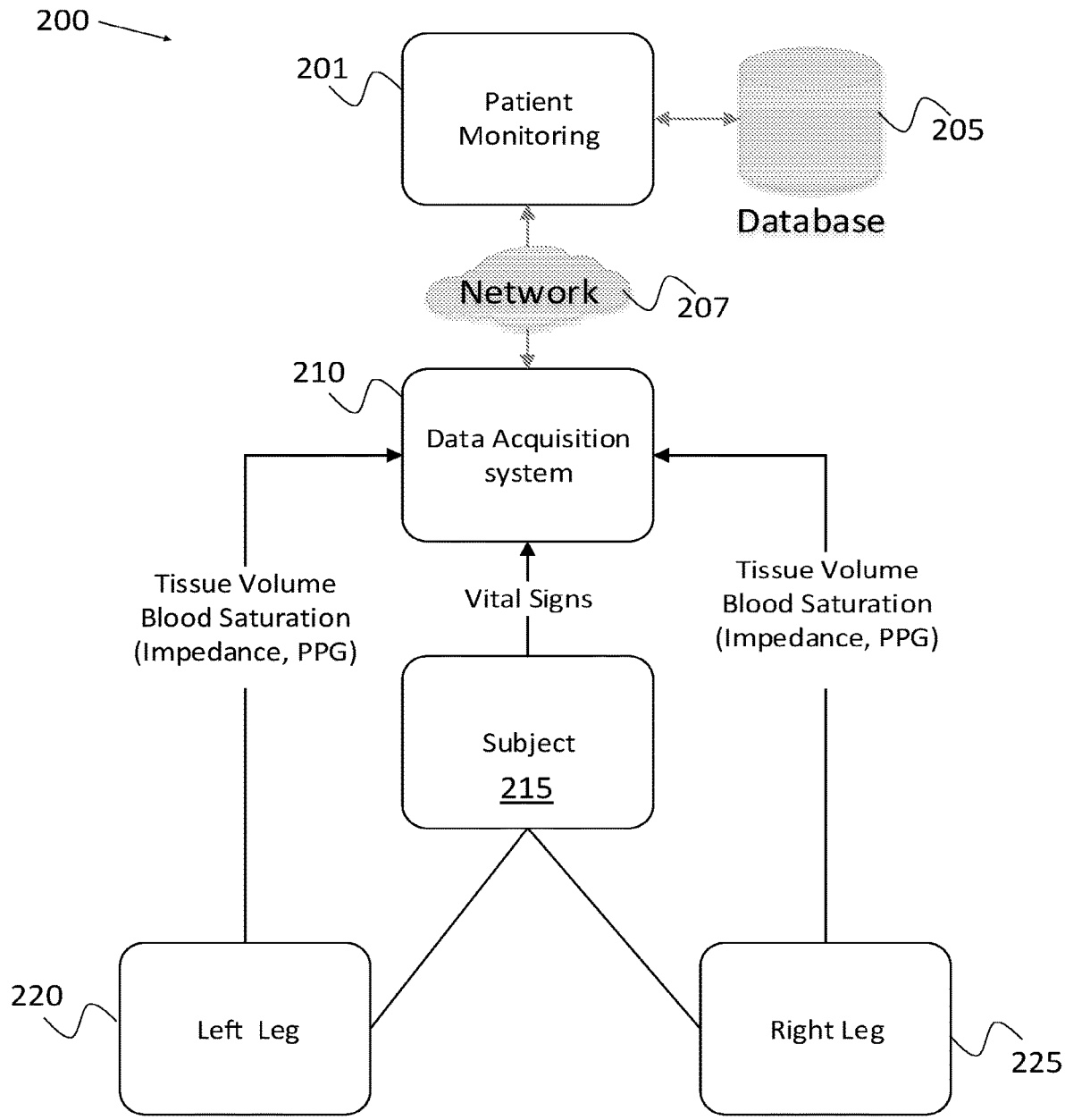
FIG. 2 shows another embodiment of a detection system, according to certain embodiments.

FIG. 2 shows another embodiment of a detection system. Detection system 200 may comprise a plurality of sensor may be connected to a subject 215. The plurality of sensors may comprise impedance measurement electrodes that may be connected above and/or below an ankle of each foot. ECG electrodes may be connected to arms or chest of subject 215 and may be used as a reference electrode placed on an abdomen of subject 215. A respiration-monitoring belt may be placed on the chest of subject 215. A pulse oximeter/PPG probe may be placed on a large toe of each leg of subject 215. A pulse oximeter probe may be placed on a finger or toe of subject 215. An accelerometer or multiple accelerometers may be placed on subject 215 to monitor motion. Detection system 200 may comprise a data acquisition system 210. Data acquisition system 210 may be configured to receive and analyze data acquired from a plurality of sensors, for example, left sensors 220, right sensors 225 and other sensors attached to subject 215. Data acquisition system 210 may communicate with a patient monitoring unit 201. In certain embodiments, the communication may be over a network 207. Detection system 200 may comprise a database 205.

Detection system 200 may allow medical staff and patients to review the monitoring results and get updates/alarms. Data processing may be performed locally, e.g. via patient detection system 201 or processing unit 110 of FIG. 1 in a distributed fashion, or may be performed with a cloud-based system. In certain embodiments, data processing may be performed using time domain analysis, frequency domain analysis, and joint time and frequency analysis. In certain embodiments, network 207 may span Personal Area Networks (PAN), Local Area Networks (LAN), Wide Area Networks (WAN), and/or the like.

The plurality of sensors of detection system 200 may be wired or wireless, and data acquisition may utilize the PAN and LAN networks to connect to the plurality of sensors. PAN embodiments may include BLUETOOTH, ANT+ wireless, or the like. LAN embodiments may include WiFi. In certain embodiments data may be encrypted and secure. In certain embodiments access to the data and the database may require authentication and proper privileges. In certain embodiments, database 205 and communication with database 205 may employ proprietary data communications protocols, employ open standards, and/or the like.

In different embodiments, the detection system 200 may enable medical staff to update a patient's status with clinical information. The clinical information may be according to analysis and quantification of external clinical evaluation using additional modalities such as ultrasound (US), computerized tomography (CT), magnetic resonance imaging (MRI) and/or the like, in order to perform "Calibration" and to improve system detection 200. In different embodiments, detection system 200 may enable medical staff to update detection system 200 with information regarding relevant procedures that the patient underwent such as operations, cauterizations, stent implantations, and/or the like. Optionally, the information may be used to update or change a chronic monitoring algorithm in order to improve detection of restenosis.

Figure 4:
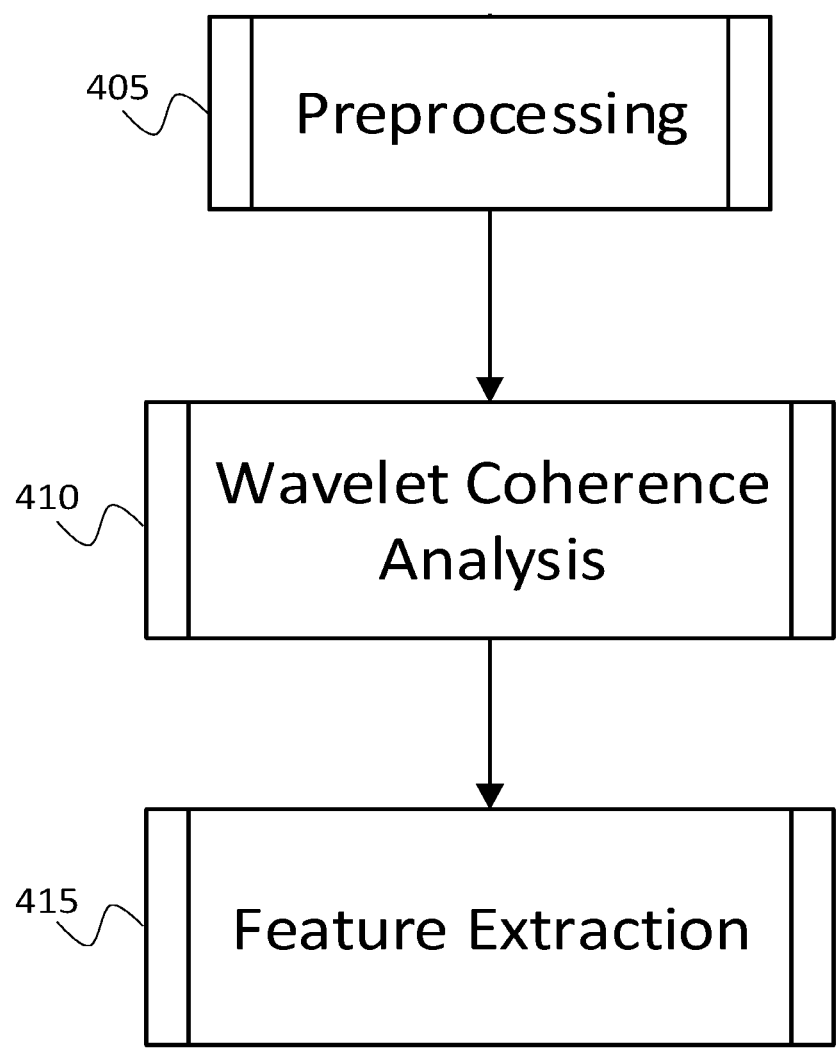
FIG. 4 shows a schematic illustration of joint time and frequency analysis, according to certain embodiments.

Referring to FIG. 4 showing a schematic illustration of joint time and frequency analysis, according to certain embodiments.

Step 405 discloses performing a preprocessing. In certain embodiment, preprocessing may comprise performing a baseline removal and high frequency noise removal by morphological operators. In certain embodiments, preprocessing may perform decimation to reduce computation time, power consumption, memory consumption and data transfer loads. In certain embodiment, preprocessing may include matching filter application of the representative signal complex in order to improve event detection rates.

Step 410 discloses performing a wavelet coherence analysis. In certain embodiment, wavelet coherence analysis may jointly test the temporal and frequency attributes of the blood volume in the subject's legs by impedance signals, which may be recorded from electrodes. The electrodes may be placed on the leg. In certain embodiment, data analysis would be performed to compare the blood volume features in each leg to those of the other leg. In certain embodiment, data analysis may be performed to compare the blood volume features of each leg to the previously acquired data recorded from that leg and the contralateral leg.

Step 415 discloses extracting features from the wavelet coherence analysis.

Figure 5:
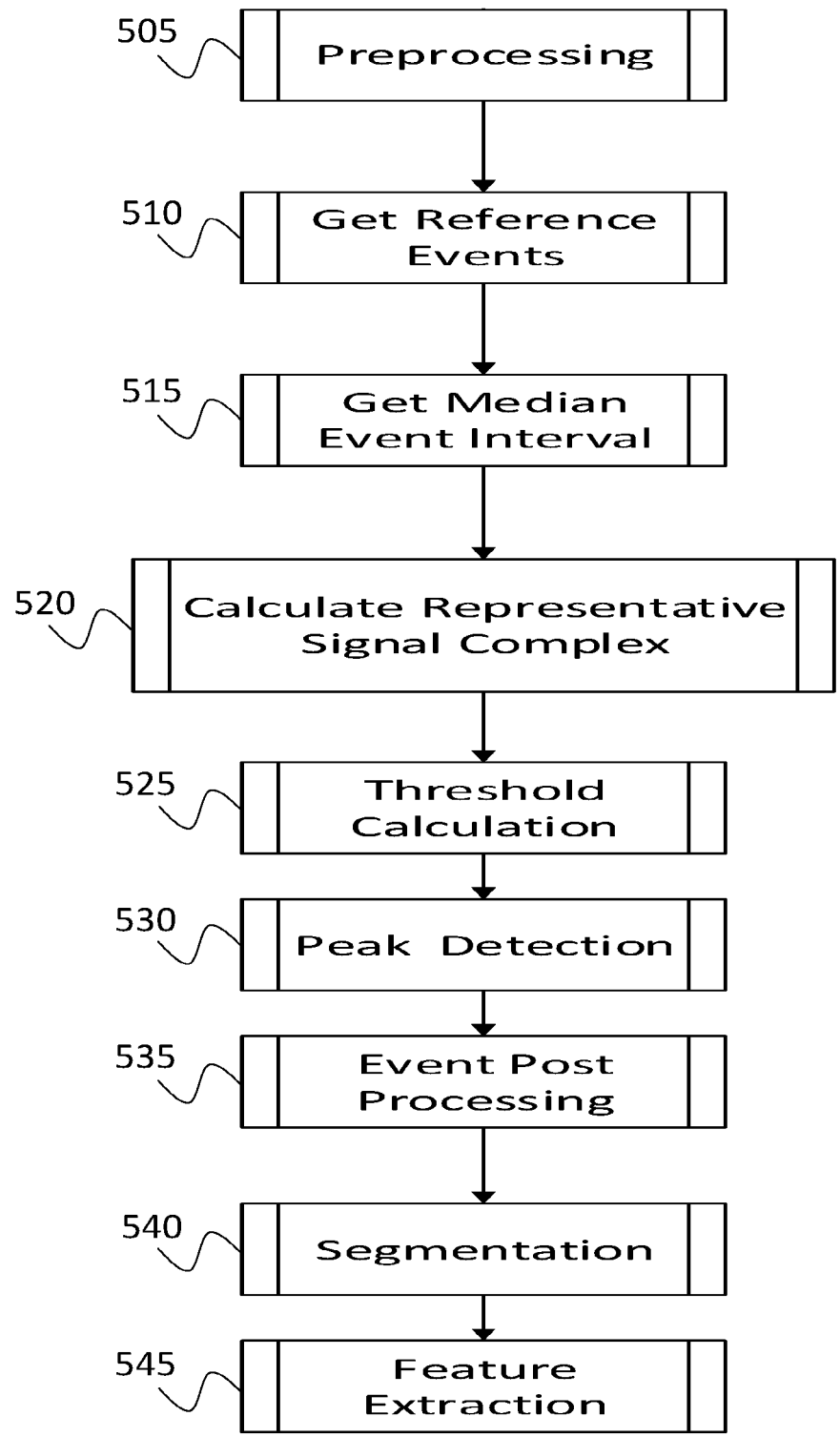
FIG. 5 shows a method of calculating and analyzing a representative signal, according to certain embodiments.

FIG. 5 shows a method of calculating and analyzing a representative signal, according to certain embodiments. Step 505 discloses performing a preprocessing. In certain embodiments, this step may be performed as Step 405.

Step 510 discloses obtaining reference events. The reference event may be any periodic wave (oscillatory event) that represents the heart cycle, such as the ECG, IPG, PPG, tonometry and others. At least two ECG electrodes may be connected to the subject's chest or arms and a reference electrode may be placed on the subject's abdomen. A respiration-monitoring belt (RIP) may be connected to the subject's chest to measure respiration. A manual blood pressure measurement cuff may be connected to one of the extremities of the subject. A photoplethysmogrphy (PPG) probe may be placed on a large toe of the leg to optically obtain a plethysmogram. A pulse oximeter probe(s) may be placed on index finger(s). The signals from the plurality of sensors 105 may be sampled over segments, e.g. 100-180 second segments at 0.5 to 2 KHz (Kilo Hertz), that may be obtained by processing unit 110. The detection system 100 may be controlled by processing unit 110. The examined subjects 215 may be allowed to relax after being attached to plurality of sensors 105.

Baseline measurements may be performed without application of pressure to the cuff.

Step 515 discloses generating median event interval. In certain embodiments, a temporal value of a heart rate (RR) interval, and RR intervals median may be applied for normalization of temporal features over changing heart rates.

Step 520 discloses calculating a representative signal complex. In certain embodiments, a representative signal complex may be calculated over set windows. A size of the set windows may be determined by the median RR interval. Windowed segments of the signal may be registered proportionally to the heart rate. In certain embodiments, the set windows may be longer than the median RR interval, e.g. 110-120% and the signals may be registered with some of the sampled signal data in a section of the set window, which precedes a concurrent heart cycle, e.g. 20% of the signal. In certain embodiments, valid heart cycles may be determined over each data set once the size of the set window and it's preceding segment lengths are determined. In certain embodiments, the representative signal complex may be calculated by aggregation into a matrix and the representative signal complex may be calculated by averaging or by calculating the median.

Step 525 discloses calculating a threshold, that determines the regions of interest that may be used for the detection of fiducial points. In certain embodiments, some acquired signals are processed and filtered. The threshold may be determined to provide an indication above or below which events may be detected, with or without additional scaling.

Step 530 discloses detecting a peak in each cardiac cycle, that may be used as the fiducial point. In certain embodiments, event detection and feature extraction may employ peak detection algorithms. Valley detection may be employed on an inverted signal. In certain embodiments, a peak heart rate may be determined according to detected ECG R-wave events.

Step 535 discloses performing an event post processing

Step 540 discloses performing a segmentation. In certain embodiments, intervals between adjacent ECG R-wave events (RR intervals) may be utilized to improve the rates of event detection percentage of other signals. In certain embodiments, segmentation may be applied for temporal feature extraction or slope calculation, for example. In certain embodiments, signal segmentation may employ change point analysis based on linear slope change; the slope change may use event detection as prior data for comparison. The number of change points might be used as input or a threshold for residual fit convergence.

Step 545 discloses extracting features. In certain embodiments, the partial arterial occlusion or vasoconstriction of the peripheral arteries may be estimated by the time and frequency attributes of the representative signal complex of a series of impedance magnitude signals by calculating the Continuous Wavelet Transform (CWT). An arterial vasoconstriction or partial arterial occlusion may be manifested by reduction of the energy magnitude of higher frequencies of the arterial frequency band, and a delay in assuming the peak temporal intensity values of the higher frequencies.

Figure 6:
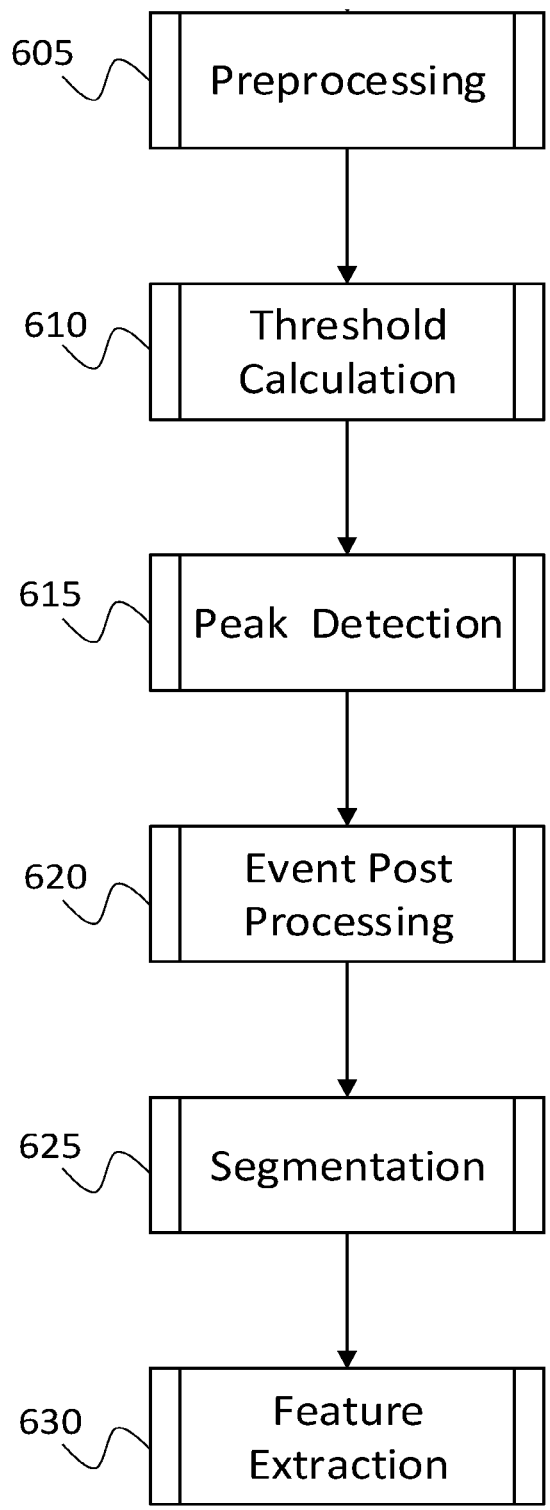
FIG. 6 shows a schematic illustration of a signal analysis method, according to certain embodiments.

FIG. 6 shows a schematic illustration of a signal analysis method, according to certain embodiments. Step 605 discloses performing a preprocessing. In certain embodiments, this step may be performed as Step 405.

Step 610 discloses calculating a threshold that specifies a region of interest, where the fiducial points may be located. In certain embodiments, this step may be performed as Step 525.

Step 615 discloses detecting the fiducial point that may be the peak of some target function that may be based on the acquired signals. In certain embodiments, this step may be performed as Step 530.

Step 620 discloses performing an event post processing. In certain embodiments, this step may be performed as Step 535.

Step 625 discloses performing a segmentation. In certain embodiments, this step may be performed as Step 540.

Step 630 discloses extracting features. In certain embodiments, this step may be performed as Step 545.

In certain embodiment, the steps disclosed herein in FIG. 4-6 may be performed in real time or near real-time.

Figure 8:
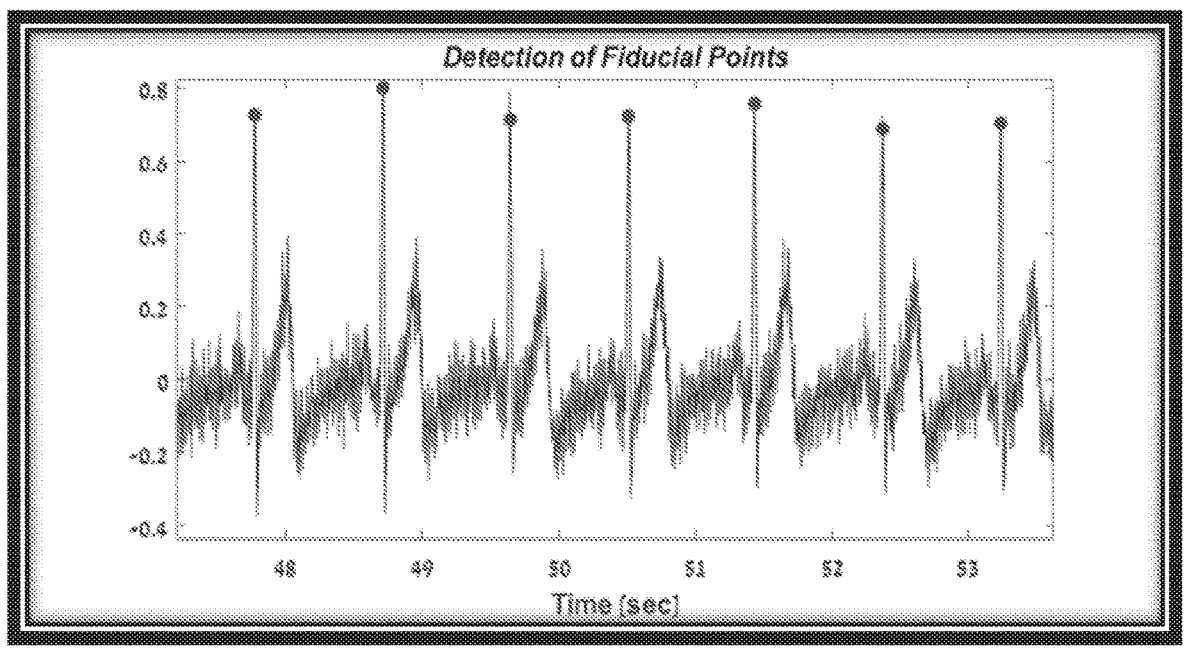
FIG. 8 shows a cycle and fiducial point detection, according to certain embodiments.

FIG. 8 shows a cycle and fiducial point detection, according to certain embodiments.

Figure 9:
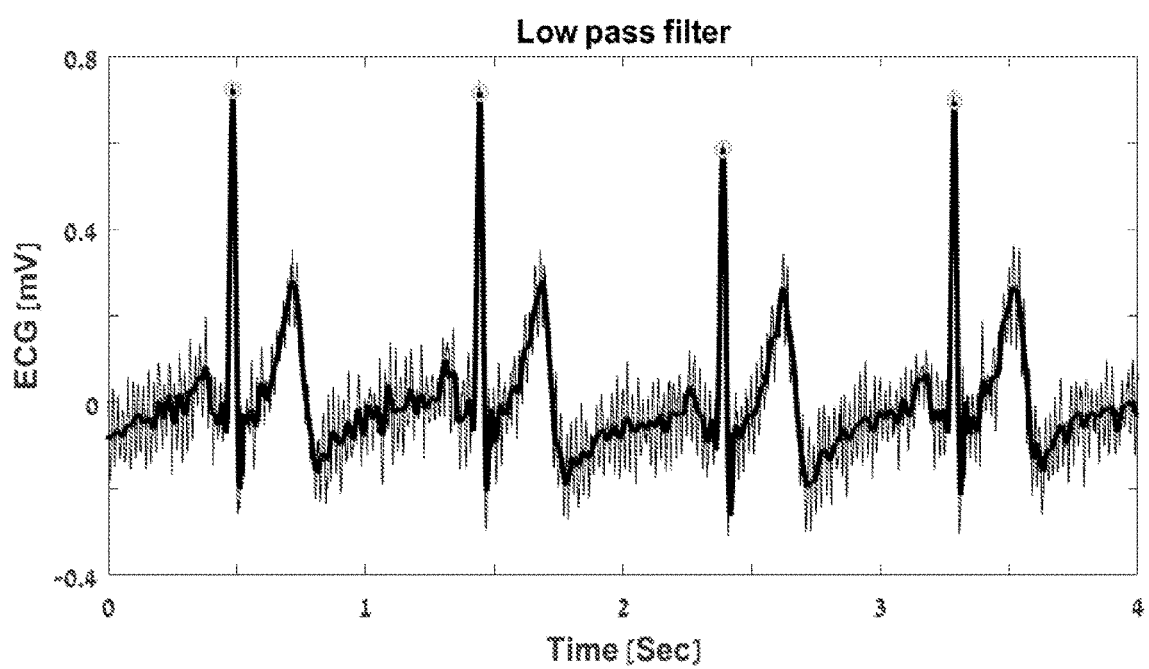
FIG. 9 shows filtering performed on obtained data, according to certain embodiments.

FIG. 9 shows filtering performed on obtained data, according to certain embodiments.

Figure 10:
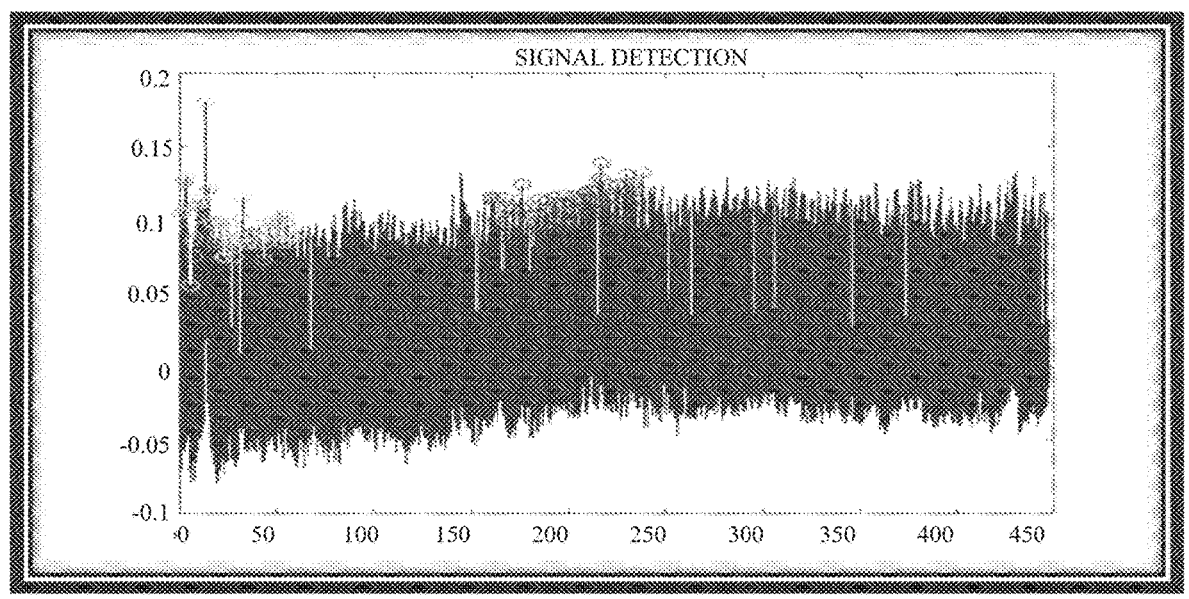
FIG. 10 shows locating fiducial points at various regions of interest along the recorded data, according to certain embodiments.

FIG. 10 shows locating fiducial points at various regions of interest along the recorded data, according to certain embodiments. For example, when the effect of inflating a cuff over one extremity of interest, the system may separately analyze cycles that are acquired at rest, before the inflation of the cuff, and cycles that are acquired when the cuff is inflated.

Figure 11:
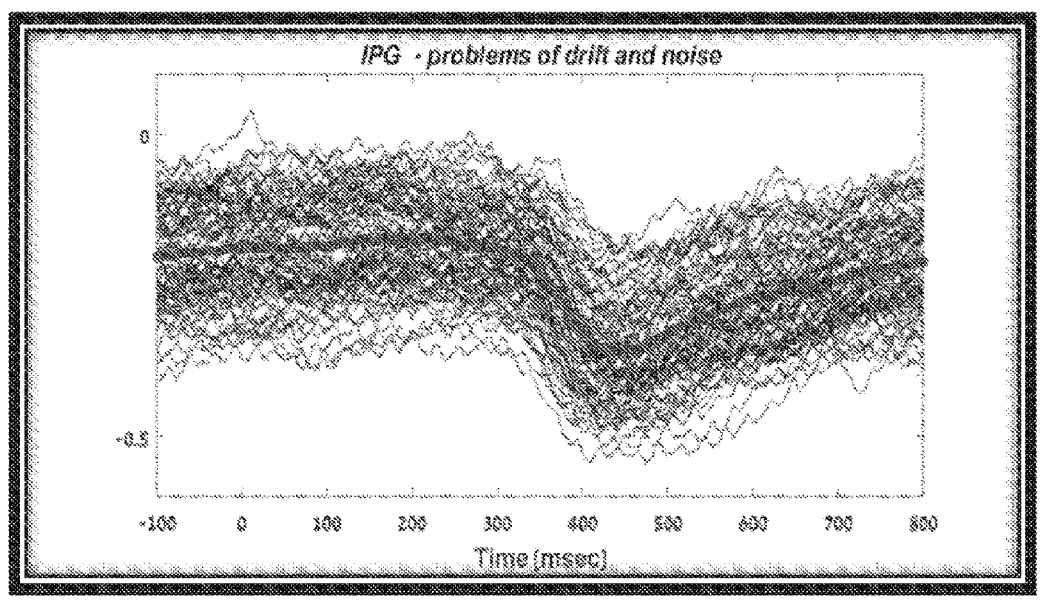
FIG. 11 shows aligning data points from obtained data, and the calculated representative signal complex according to certain embodiments.

FIG. 11 shows aligning data points from obtained data, according to certain embodiments. This figure presents an ability of the system to handle noise and large drift in a baseline of the acquired signals.

Experimental Results

Figure 7:
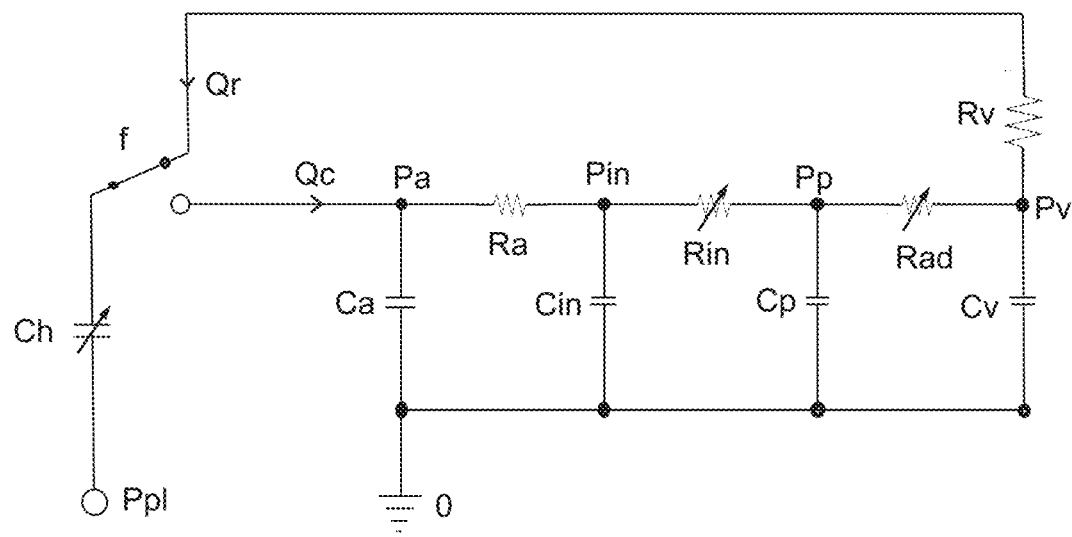
FIG. 7 shows an adaptive control model, according to certain embodiments.

Referring to FIG. 7, an adaptive control model may represent the effects of a partial and focal occlusion of a large artery on tissue perfusion. The partial occlusion of a large artery, and the increase in its resistance ($R_{in}$) may be associated with a compensatory decrease in the arteriole resistance ($R_{ad}$), by the autonomous and peripheral control of blood perfusion, in order to maintain the normal perfusion of the microvasculature. At early stages, when there is adequate compensation, it may be shown that the average perfusion may be maintained as long as:

$$R_{in}+R_{ad}=\text{const} \tag{1}$$

Under normal conditions $R_{in} \ll R_{ad}$, but as $R_{in}$ increases $R_{ad}$ decreases. ABI may be close to 0.5 when $R_{in}$ is almost equal to $R_{ad}$. The rate constant of the transfer function of the arterial tree under these condition is given by:

$$\tau = \frac{C_p R_{ad} R_{in}}{R_{in}+R_{ad}} \tag{2}$$

Under normal condition the resistance to flow in the large arteries ($R_{in}$) is negligible, and the peripheral perfusion is regulated at the level of the arterioles. The arterioles provide the adaptive control of the tissue perfusion, and the resistance of the arterioles ($R_{ad}$) is high and the total peripheral resistance is dominated by $R_{ad}$, and $R_{ad} \ggg R_{in}$.

The peripheral arteriole system aims to preserve the adequate peripheral perfusion in the presence of various changes in the blood pressure and demands. The same applies to the development of obstructive lesions in the vascular systems. The peripheral perfusion remains practically constant, at rest, despite the development of small partial obstruction in focal points along the large arteries. The compensation for an increase in $R_{in}$ is by decreasing $R_{ad}$—the arterioles resistance. This compensation may attempt to hold the precapillary pressure at a microcirculation within the normal level.

Changes in the compliance of the arterial system have a smaller effect. The changes in the compliance of the arterioles are negligible compared to the compliance of the large peripheral arteries ($C_p$). The compliance of the arteries decreases with age, however at a very slow rate. Moreover, while focal obstructions along the large arteries have a large effect on $R_{in}$, they have only a small effect on $C_p$, since the compliance is determined by the volume encompassed within the entire large vessels. Multiple lesions can exist and atherosclerotic disease affects the vessels compliance, but the rate of change in the compliance is significantly lower than the dramatic changes that can occur in the resistance ($R_{in}$).

The increase in $R_{in}$ and the adaptive changes in $R_{ad}$ affect the rate constant of the arterial system. Consequently, it modulates the upslope and downslope of the perfusion wave and its power spectrum content. Under normal conditions, the pressure in the arterioles system is identical to that in the large arteries (since the pressure gradient along the large artery is negligible); progressive occlusion turns the system into a low pass filter with lower cutoff frequency. As $R_{in}$ increases and $R_{ad}$ decreases, the high frequency harmonics are attenuated.

As $R_{in}$ increases and Rad decreases there will be an increase in the mean difference between the aortic pressure ($P_{in}$) and the distal arterial pressure ($P_a$), which will lead to continuous, almost DC current through $R_{in}$. This mechanism predicts the development of a delay in the arrival of the perfusion wave.

Thus, the analysis of the adaptive control model may predict change in perfusion dynamics, in the shape of the waves, in the power-spectrum, and the development of a delay in the time of arrival of the peak of perfusion wave.

Figure 3:
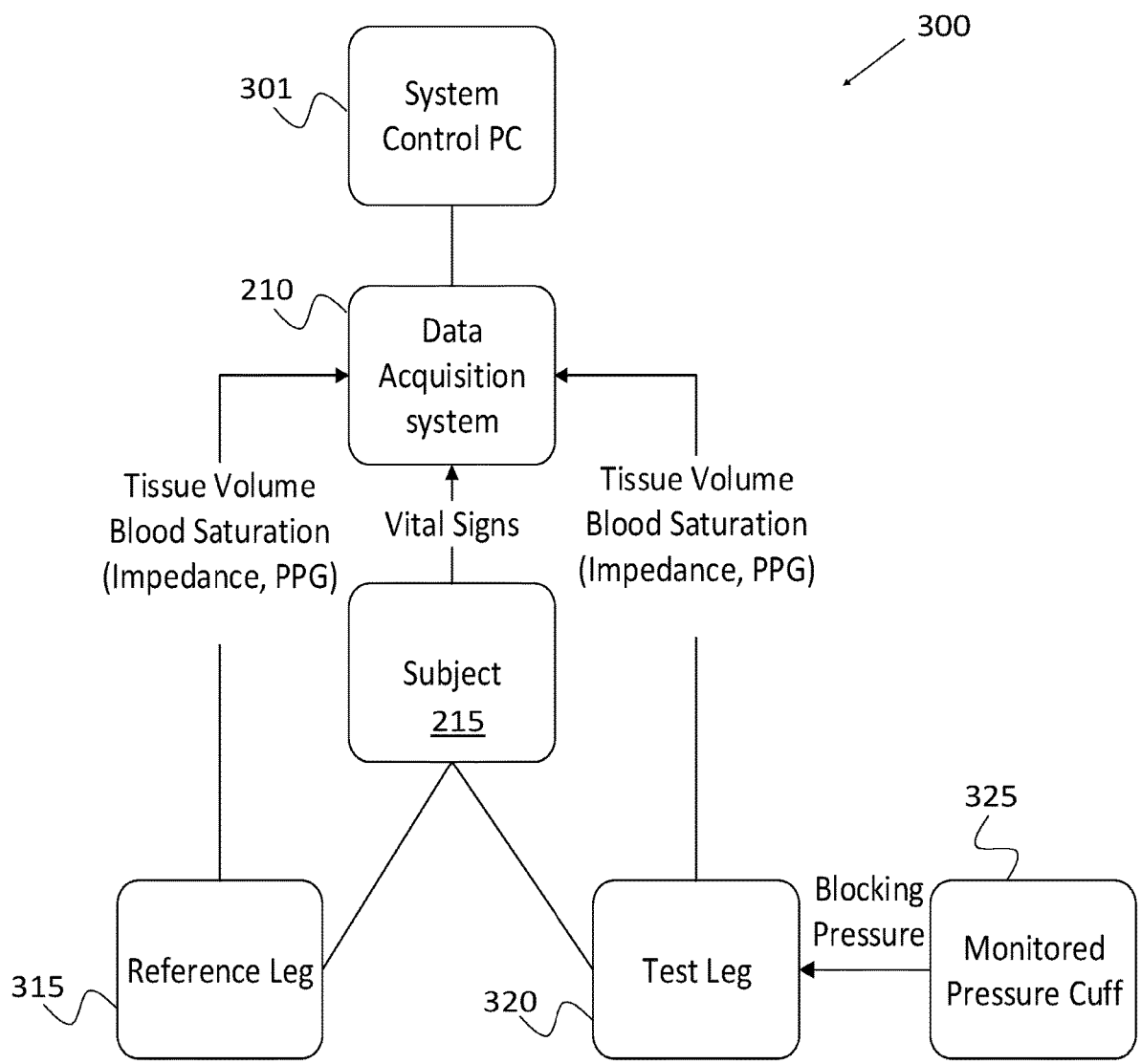
FIG. 3 shows an experimental setup to emulate vasoconstriction through pressure application, according to certain embodiments.

Reference is now made to FIG. 3, which illustrates an experimental setup to emulate vasoconstriction through pressure application, according to certain embodiments. Data acquisition system 210 may be connected to reference leg sensor 315 and to test leg sensors 320. To a tested leg, a monitored pressure cuff 325 may be connected. The monitored pressure within the cuff 325 may be used for the selection of regions of interest (e.g. baseline, certain pressure level/mode of perturbation) for the analysis, as depicted in FIG. 10. Data acquisition system 210 may provide the data measurements to a system control processing unit 301. The system control processing unit 301 may analyze the data to determine whether the subject 215 has a change in perfusion in a lower extremity.

In the feasibility study on human volunteers, e.g. thirteen volunteers (n=13), partial arterial occlusion was modeled by inflating a cuff of a regular pressure monitor around a leg of the volunteer, for a short time interval, e.g., within a range time range of 1-3 min. The volunteers were laid supine on medical examination beds and instructed to breathe regularly and refrain from movement. At least two sets of of IPG sensors 104, e.g. at least two sets of IPG electrodes, were connected above and below the ankle of both feet of each volunteer.

Partial arterial occlusion was modeled by application of: 30, 60 and 90 mmHg pressures to the cuff. Data was acquired under normal condition (without obstruction), duing the obstruction and also during the recovery. The period of partial obstruction lasted three minutes (one hundred and eighty seconds), and it began after a period of habitation and stabilization post pressure application. Between recordings, the pressure was released from the cuff and the patients were allowed to recover for ten minutes while lying supine on the examination bed.

Before referring to the graphs with ECG data (from FIG. 11 onwards), it is important to understand features of the invention that provide significant improvements over the prior art.

As is well known in the art, different portions of the waves in an ECG are referred to, in order from left to right in the ECG, as P, Q, R, S and T waves. The P wave represents atrial depolarization, which results in atrial contraction (atrial systole). The T wave represents the repolarization or recovery of the ventricles. The Q wave is any downward deflection immediately following the P wave. The R wave follows the Q wave as an upward deflection, and the S wave is any downward deflection after the R wave. The T wave follows the S wave.

Although the invention is not limited to any theory, the following is an explanation of the behavior of the perfusion wave as observed in many experiments.

The rise of the perfusion wave consists of two phases, an initial (or first) slow phase followed by a subsequent (or second) faster phase (that is, faster than the first phase). The transition point between these two phases is the point where the acceleration (second derivative) is maximal (as seen in FIG. 10A).

Figure 10A:
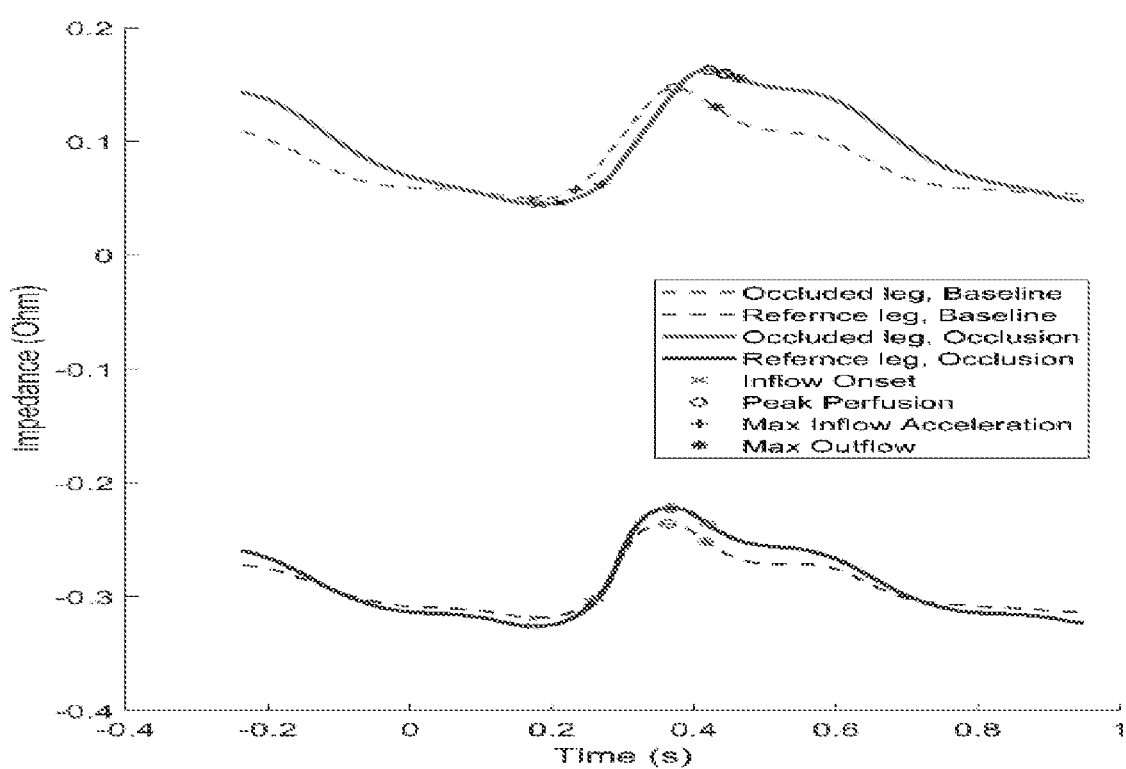
FIG. 10A is a graphical illustration of various time points in the perfusion wave propagation.

In FIG. 10A, in the upper graph, the dotted line is the plot of the occluded leg baseline and the solid line is the plot of the occluded leg during occlusion. In the lower graph, the dotted line is the plot of the reference leg baseline and the solid line is the plot of the reference leg during occlusion. In both upper and lower graphs, x are measured points of inflow onset, o are measured points of peak perfusion, + are measured points of maximum inflow acceleration, and the asterisk signs are measured points of maximum outflow.

Figure 10B:
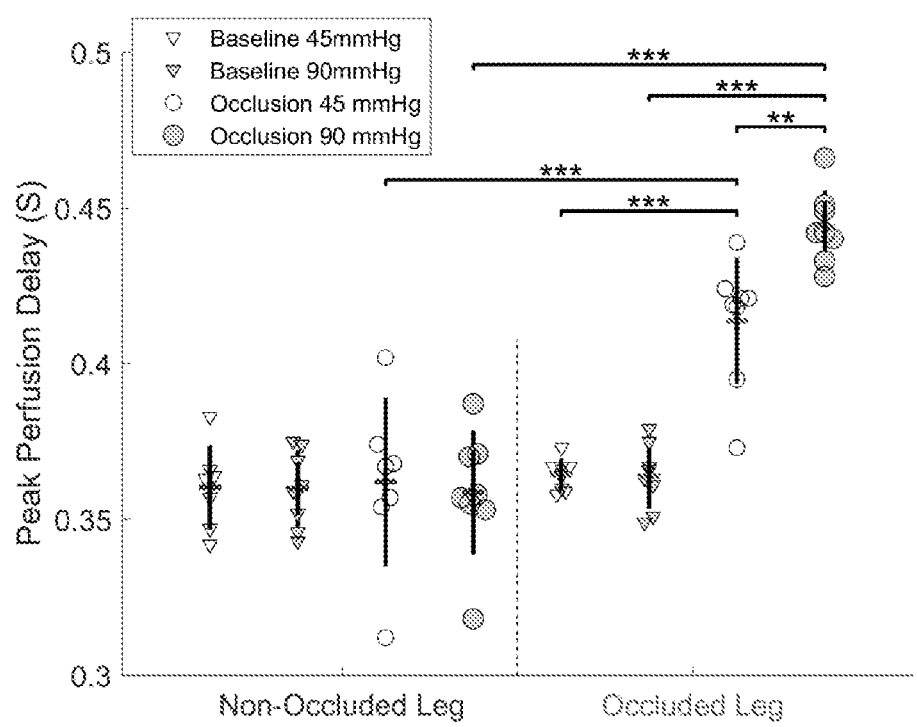
FIG. 10B is a graphical illustration of peak perfusion delay.
Figure 10C:
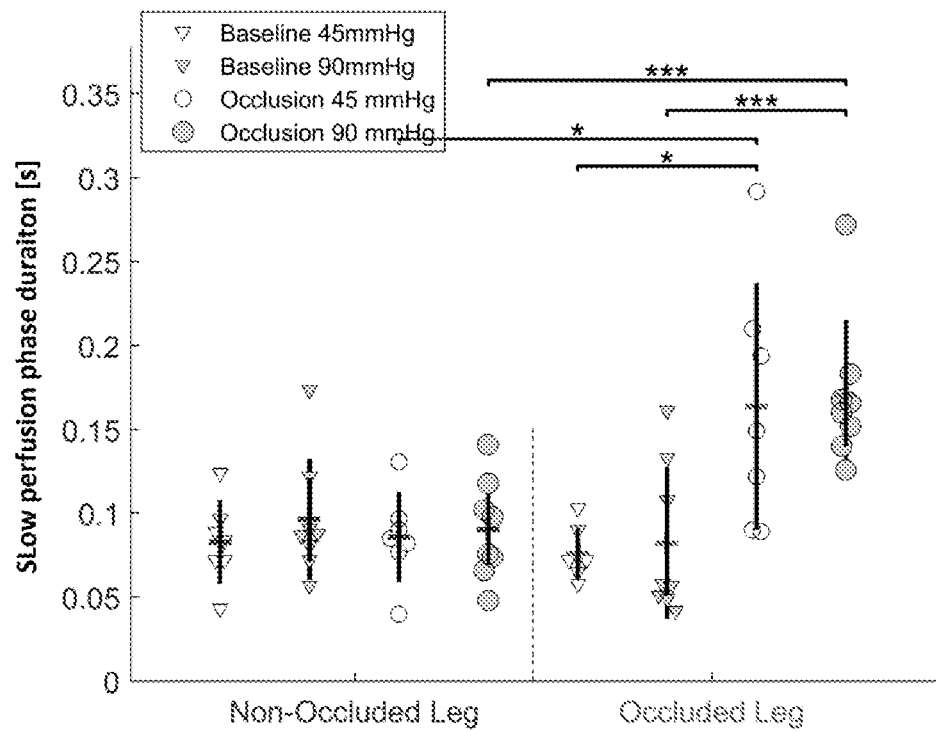
FIG. 10C is a graphical illustration of changes in the first slow phase of the perfusion wave.

The peak perfusion delay (as seen in FIG. 10B) is a novel and inventive tool for indicating the presence of arterial or venous obstructions (or lesions, the terms being used interchangeably herein). Surprisingly, the inventors have observed that a major cause for the increase in the peak perfusion delay is the prolongation of the initial slow phase. The changes in the initial slow phase are shown in FIG. 10C.

The peak perfusion delay includes: (a) the interval from the R wave to the perfusion onset, also referred to as the pulse-transit time; (b) the slow phase of the perfusion wave; and (c) the fast and steep phase of the perfusion wave. Surprisingly, the inventors have observed that (a) and (c)— the pulse transit time and the fast phase—are not statistically significant, contrary to prior art thinking which expects the pulse transit time to be faster in a stiffer blood vessel. Without being bound to any theory, the inventors believe the surprising delay is due to the transition from elastic energy to kinetic energy in the occluded region and then back to elastic energy. Whatever the explanation, the existence of two phases and the prolongation of the first phase are the important indices that should be quantified.

Figure 10D:
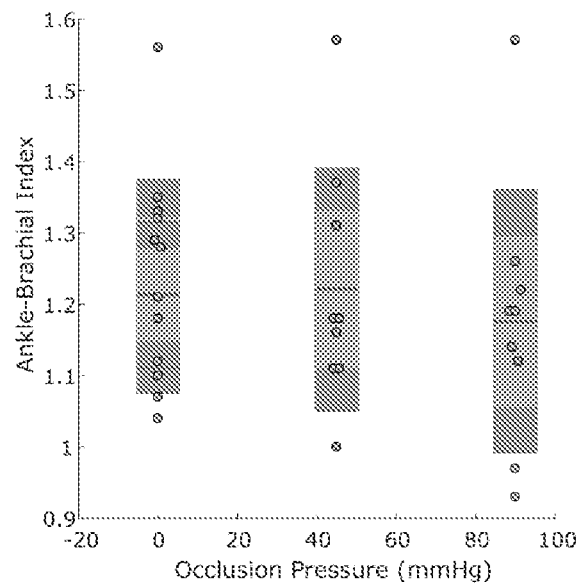
FIG. 10D is a graphical illustration that shows there are no changes in the ABI, that is, the ABI fails to detect occlusions.

FIG. 10D and Table 1 (FIG. 10H) provide evidence that the ABI fails to detect the existence of obstruction, as opposed to the method of the present invention, which successfully uses the perfusion propagation delay to detect the existence of obstruction.

Figure 10E:
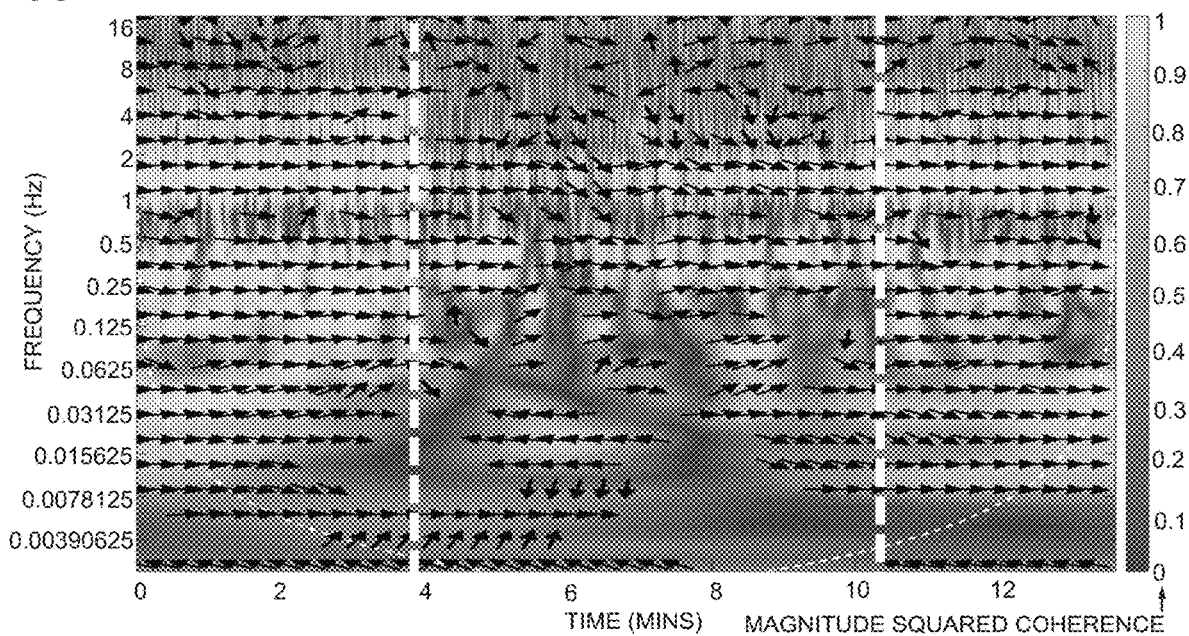
FIG. 10E is a graphical illustration of quantification of changes in the time-frequency domain, wherein the portion of FIG. 10F labeled "A" is the wavelet coherence plot during 90 mmHg occlusion (the region in the graph between the two vertical dotted lines) and the portion labeled "B" is the phase shift at the different bands (1 to 2 Hz, and 1 to 6 Hz bands), between baseline and occlusion, at two levels of occlusion pressures: 45 mmHg on the left and 90 mmHg on the right.
Figure 10E:
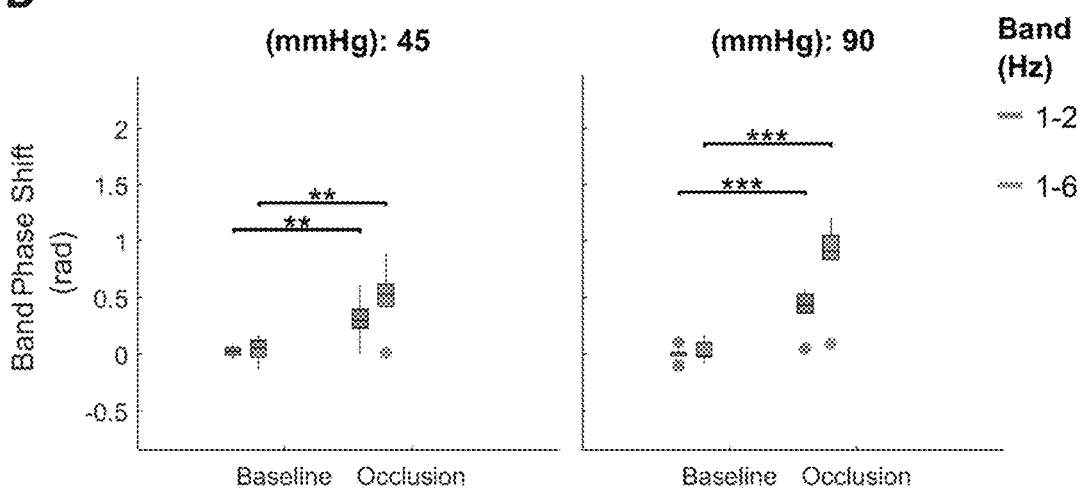
Figure 10F:
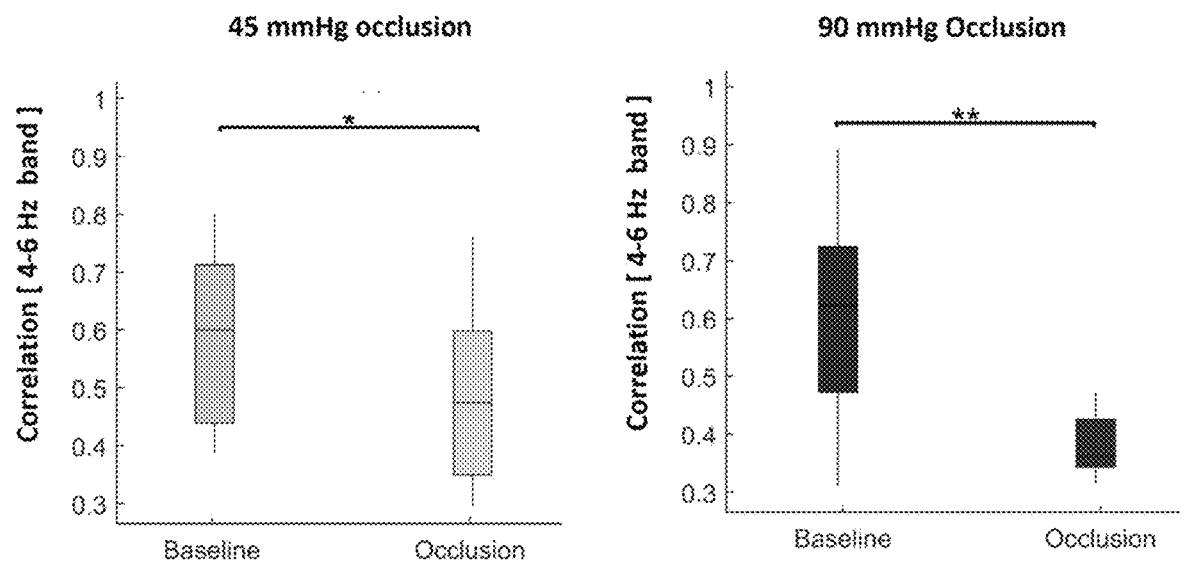
FIG. 10F is a graphical illustration of estimation of the changes in the correlation amplitude, at the frequency band of 4 to 6 Hz (the high frequency band) in response to two levels of partial occlusion: 45 mmHg on the left and 90 mmHg on the right (from the analysis of the time-frequency domain)
Figure 10G:
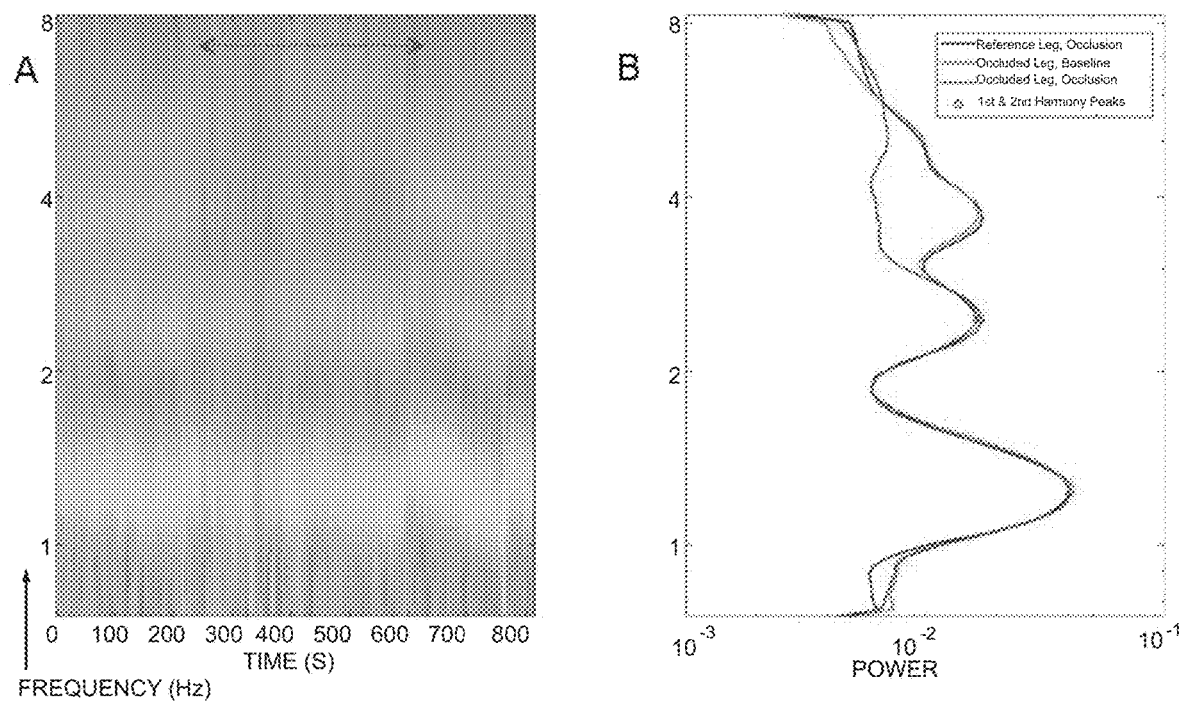
FIG. 10G is a graphical illustration of the significant effect of occlusions on the high frequency band, wherein the portion of FIG. 10G labeled "A" is the time-frequency domain and the portion labeled "B" is the estimated power spectrum (note the drop in the power around 4 Hz; the y axes of both plots were aligned to present the same frequency range)

FIGS. 10E, 10F and 10G illustrate the advantages of using the time-frequency domain to measure the perfusion propagation delay.

FIG. 10E presents the changes in the phase shift at the different frequency bands. FIG. 10F presents the utility of using the correlation between both legs of the subject at the different frequencies. FIG. 10G presents changes in power, especially at the high frequency band.

Quantification of the frequency domain enables analyzing and quantifying the changes in the transfer function, such as the development of different phase delays at different frequencies and the attenuation of the high frequency bands.

The time-frequency domain enables differentiating between the cardiac band and the respiratory band, which can thus differentiate between arterial problems and venous problems.

The correlation between the two legs of the subject in the time-frequency domain can increase the sensitivity and can also define the location. Symmetrical changes indicate that there is a problem in the aorta before the bifurcation. Asymmetrical changes can identify which leg is more severely affected.

Phase and frequency changes, unlike amplitude changes, are less sensitive to artifacts and to the precise location of the electrode. Thus, measuring phase and frequency changes can be used for repeated monitoring over time and in home use.

Figure 14:
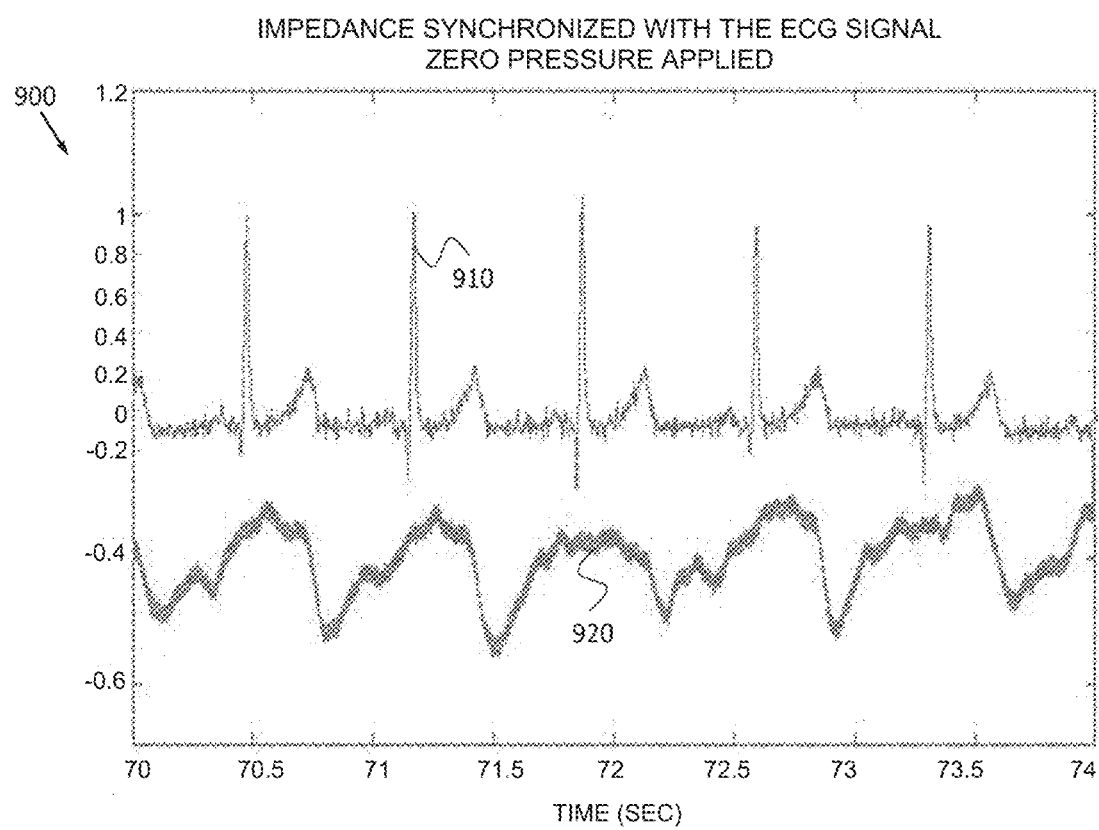
FIG. 14 shows a graph illustrating results obtained, according to certain embodiments.
Figure 15:
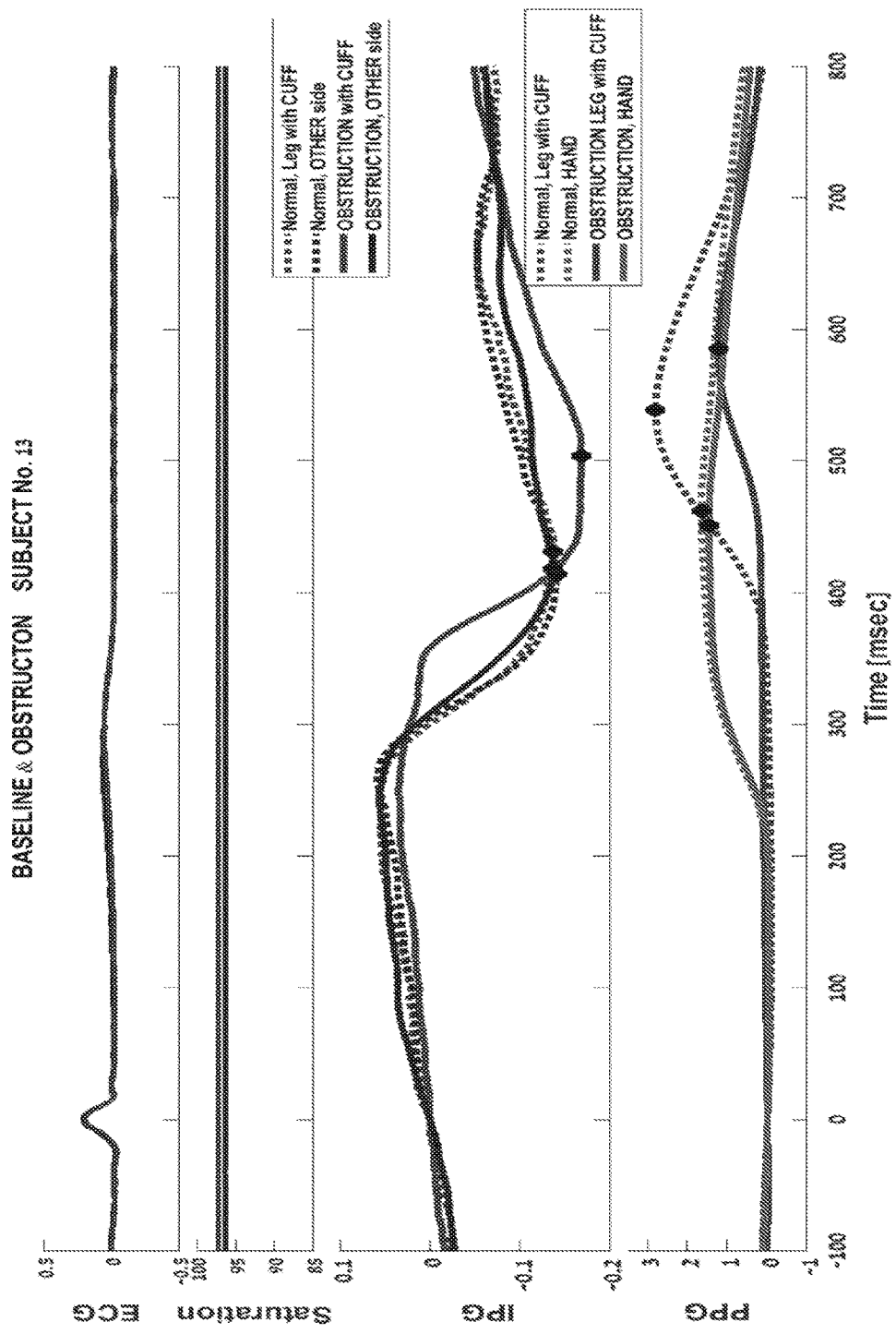
FIG. 15 shows a graph of change in results over time, according to certain embodiments; and, FIG. 16 shows a graph illustrating results obtained from thirteen subjects, according to certain embodiments.

The peaks in the normal IPG graphs in FIGS. 11, 14 and 15 appear "inverted" (facing down) vs. the ECG R-waves (facing up) since the flow of blood increases the blood volume and decreases the impedance. A normal IPG wave under normal baseline condition (without obstruction) is characterized by a fast transient. Partial arterial obstruction, by inflating the cuff to 30 and 60 mmHg, yielded the following characteristic changes: no significant change in the pulse transit time (from the R wave to the beginning of the inflow), an appearance of a delay in the first phase of the perfusion wave, delay in the time to peak perfusion. These changes are also described in FIG. 10A. In addition there is flattening of the shape of the curve, deceleration of the downslope, and all the transient oscillatory wave becomes smoother (loss of high frequencies).

Wavelet coherence analysis was employed in order to study the hypothesis stated above, by jointly testing the temporal and frequency attributes of the impedance signals of the tested leg which was exposed to blocking pressure and the reference leg which was not subjected to blocking pressure.

Figure 12:
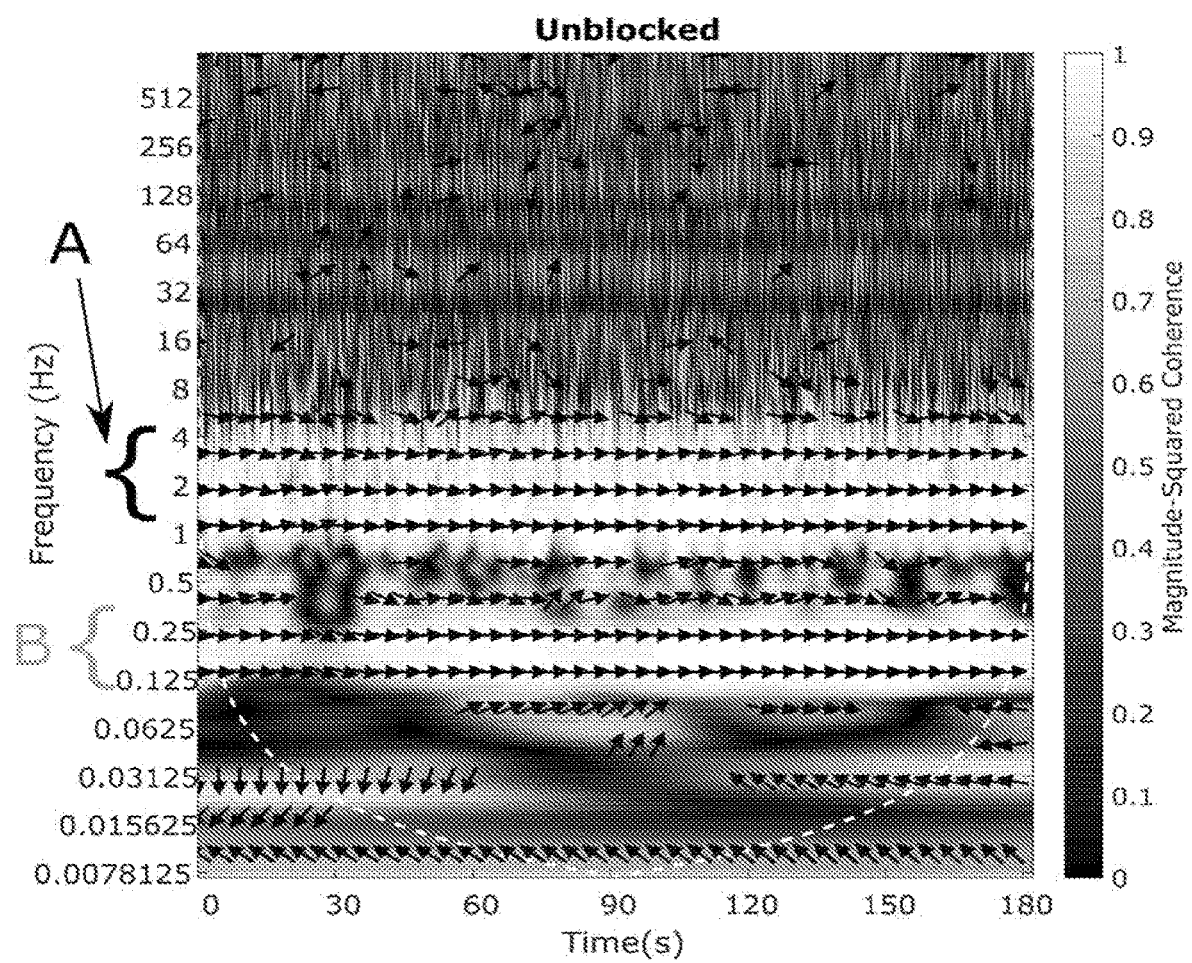
FIG. 12 shows a graph illustrating a wavelet coherence analysis of impedance signals without application of a blocking pressure, according to certain embodiments.

Reference is now made to FIG. 12, which shows a graph illustrating a wavelet coherence analysis of impedance signals without application of a blocking pressure, according to certain embodiments. Baseline is defined as the situation when no blocking pressure was applied on either leg. The signals of each leg demonstrated high coherence throughout the entire measurement duration. This is indicated in two frequency bands: 1-6 Hz (A in FIG. 12) that relates to the heart rate and the propagating pulse wave, and 0.125-0.5 Hz (B in FIG. 12), which is explained by the respiration modulation of the arterial and venous flows.

The estimated phase difference in the arrival time of the blood pulse is illustrated by the black arrows shown in FIG. 12. When no blocking pressure is applied, the estimated pulse arrival times are suggested to be very close as indicated by the phase difference, which is close to zero. This behavior is noticed across both frequency ranges. Slight phase fluctuations around zero are noticed which could indicate close symmetry of the healthy subject's legs without application of blocking pressure.

Figure 13:
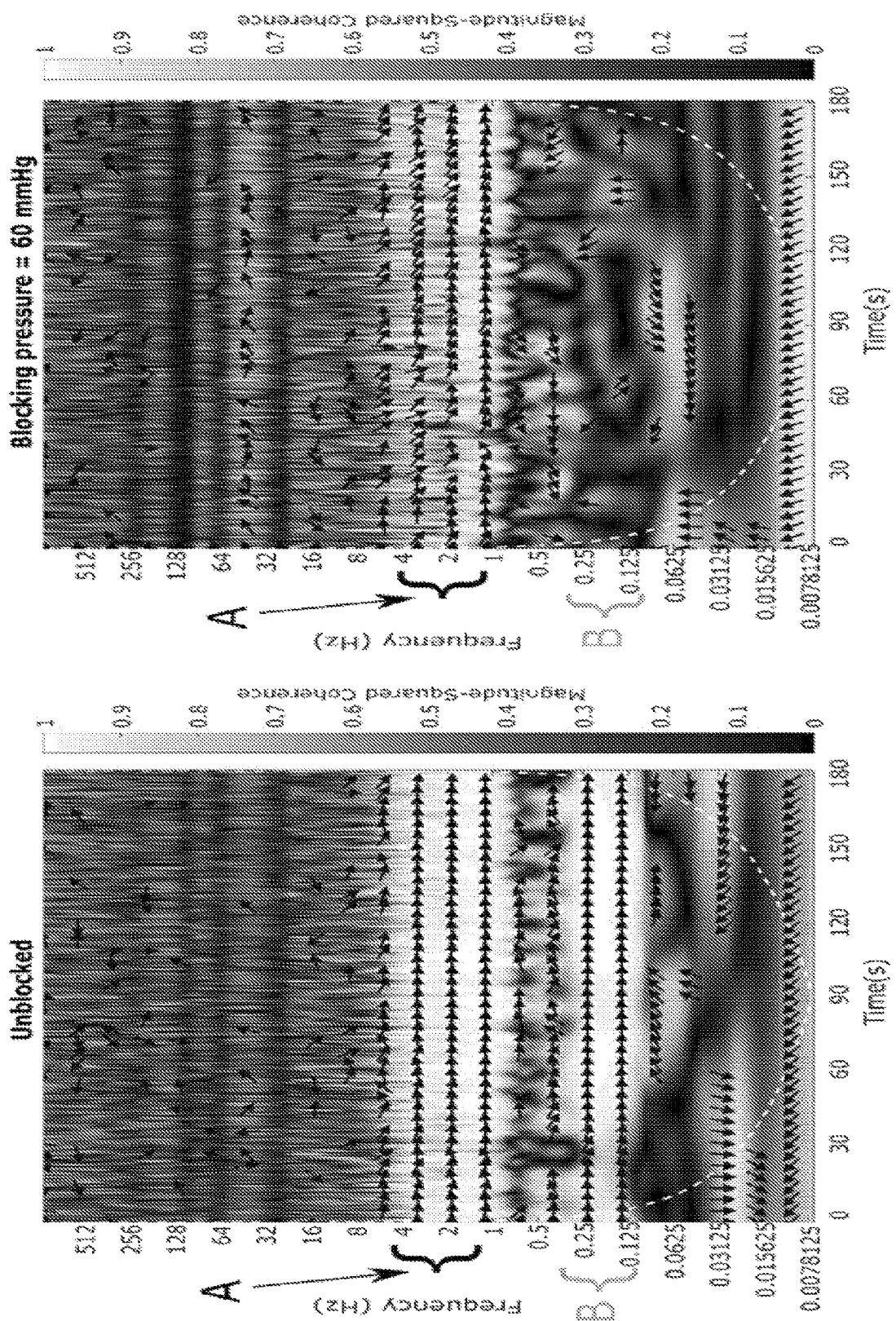
FIG. 13 shows experimental observations utilizing the wavelet coherence analysis of impedance signals under application of sixty millimeters of mercury blocking pressure, according to certain embodiments.

FIG. 13 illustrates experimental observations utilizing the wavelet coherence analysis of impedance signals under application of sixty millimeters of mercury blocking pressure, according to certain embodiments. The figure presents the effects that partial obstruction of the arteries or the veins on the monitored wavelet coherence at the various frequency bands:

Referring to FIG. 13, the coherence at the frequency range of 0.125-0.5 Hz was no longer observed. Breathing and changes in the thoracic cavity pressure affect both the venous return and the arterial pressure. Inspiration and decrease in the intra-thoracic cavity pressure increases the venous return to the right ventricle, and simultanously the inspiration decreases the stroke volume and the arterial pressure due to the decrease in the venous return to the left ventricle. At the applied pressure the inflated cuff has a minor effect on the modulation of the arterial pressure but a large effect on the venous return from the leg. Thus the disappearance of the B band at the low frequencies in FIG. 13 during the inflation of the cuff is mainly due to the obstruction of the venous drainage. Thus the system can differentiate between arterial and venous problems that may affect tissue perfusion.

At the circulatory frequency band (Band A in FIGS. 12 and 13), the occlusion leads to lower correlation at the high frequency range. The analysis at the frequency domain is less sensitive to changes in the absolute amplitude, as it is normalized to the maximal amplitude at the baseline heart rate. The analysis reveals the attenuation of the high frequency harmonics (above 2 Hz). Thus, the analysis at a frequency domain may improve sensitivity and is less sensitive to changes in the amplitude.

An additional indication for the development of partial obstruction at the level of a large artery is the increase in a phase difference of the IPG of PPG signals between the two legs, which may be marked by the black arrows. The system can measure and quantify the decrease in the correlation of the compared signals. The development of obstruction would first manifest by reduction of coherence in higher frequencies and would later affect lower frequencies upon progression. Thus, the analysis of the wavelet coherence between the two legs of subject 215 may be sensitive to the development of asynchrony due to arterial obstruction at a level distal to the bifurcation of the abdominal aorta into the two iliac arteries.

Detection system 200 may assist in monitoring patients with a high risk of developing occlusion in blood vessels and in need of home monitoring and close supervision, e.g. diabetic patients. Detection system 200 may assist in monitoring patients that underwent a medical procedure (e.g. amputation, arteries implantation) and require tight perfusion measurements and monitoring, during hospitalization (in hospitals) and following the discharge (at home). Detection system 200 may assist in hospital monitoring of intensive care patients—as additional indirect index to changes in cardiac output and in patient with various types of shock (septic, cardiovascular, hemorrhagic and other systemic diseases)

Although the exemplary embodiments described herein focus primarily on peripheral arterial disease due to the simple accessibility of the peripheral arteries and peripheral organs (legs), detection system 100 may be implemented to monitor any tissue requiring continues perfusion monitoring.

Reference is now made to FIG. 14, which shows a graph illustrating results obtained, according to certain embodiments. Graph 900 shows an ECG signal 910 and an impedance signal 920. Impedance signal 920 shows a change in blood volume and feeding of tissue. Peaks of ECG signal 910 relate to the onset of contractions of the heart and injection of blood immediately afterwards. There is a small delay in impedance signal 920 due to the time it takes the blood to flow in the blood vessels. Under normal conditions, the signals are fast and sharp, e.g. a sharp decrease and immediately a sharp increase.

FIG. 15 illustrates a graph of change in results over time, according to certain embodiments. The signals shown in the graph were recorded over fifty cycles for removal of noise. ECG as shown in the upper trace does not change between obstruction (solid line) and non-obstruction (dashed line) measurements. The oxygen saturation graph (the second trace) shows that an obstruction does not cause a reduction of oxygen saturation. The IPG plots (the third plot from the top) shows changes between rest without obstruction (dashed lines) and an obstruction (solid line). When both legs, e.g. the non-obstructed leg (thin dashed line) and the obstructed leg with the inflated cuff (thick dashed line), are at rest they are practically identical. There is no significant difference in the non-obstructed leg between the recording at rest (thin dashed line) and the recording when pressure is applied to the cuff on the other leg (thin solid line). However, the obstructed leg presents significant shift (delay) and changes when cuffed (thick solid line) with flattening of the peak region over a longer period of time. The botton trace presents the PPG recordings from the hand (thin lines) and the toe (thick lines) at rest (dashed lines) and during obstruction (thick lines). As expected there are no significant changes in the recordings from the hand between rest and obstruction. However, obstruction causes significant delays and changes in the shape of the signals that were recorded from the toe (thick solid line) relative to the signals that were recorded before obstruction (thick dashes line).

Figure 16:
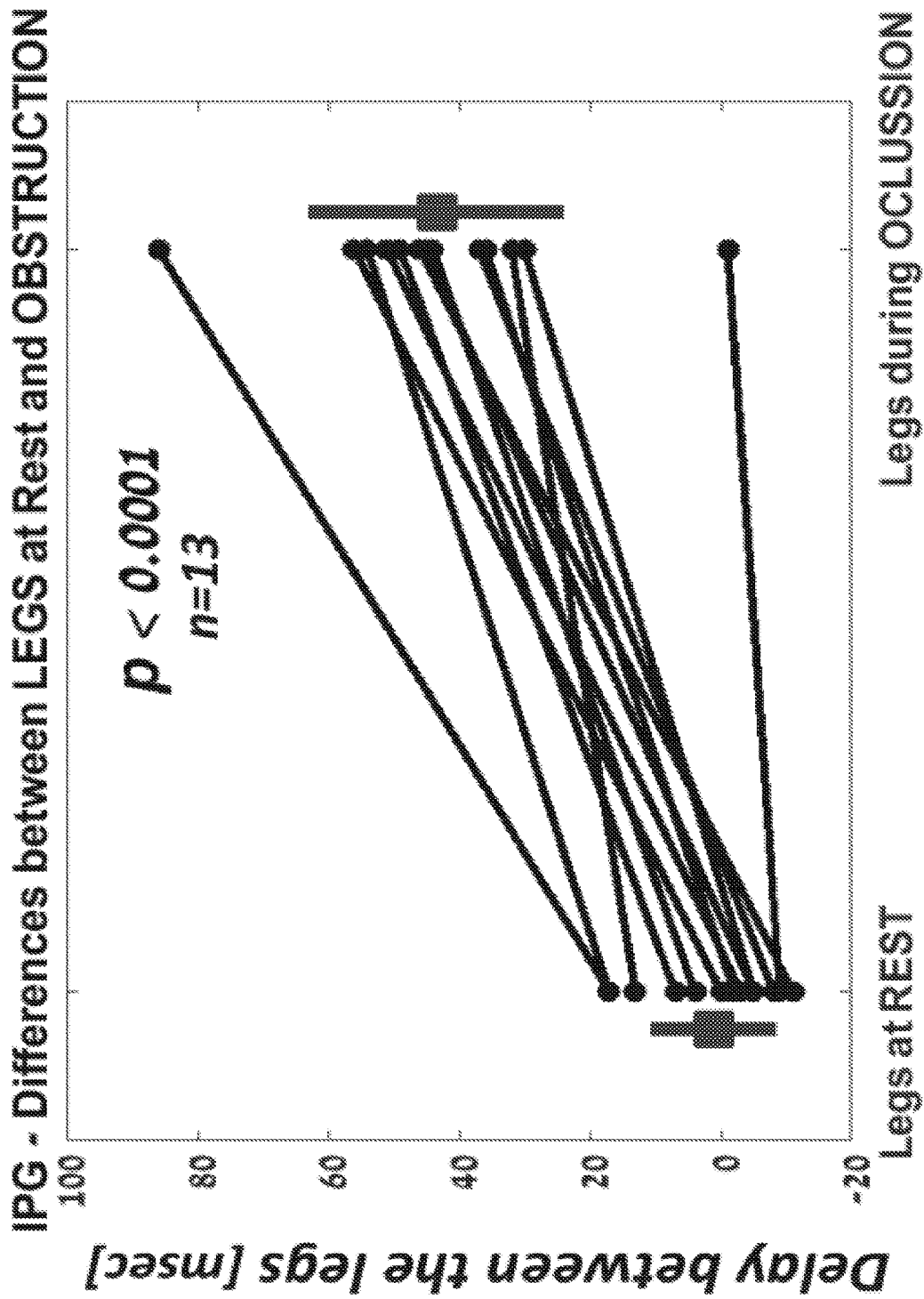

FIG. 16 illustrates a graph of results obtained from thirteen subjects, according to certain embodiments. The graphs shows one novel index, the difference in the delay in the IPG wave between the two legs, for thirteen trials, where each line represents one subject at two different conditions: normal and obstruction by inflation of a cuff around the leg. The graph shows the amount of time between pulses reaching each leg, e.g. obstructed and non-obstructed. During rest there is no significant difference between the legs, e.g. the pulse reaches both legs at the same time. During oclussion there is a larger delay in the obstructed leg while there is no change in saturation and in feeding, which enables detecting additional clinical symptoms.

TABLE A

Results of the experiment are summarized in Table A:

| 1. | 2. SATURATION | | 3. IPG | | | |
| | | | 6. Rest | | 8. OBST | |
| | 4. Rest 10. | 5. OBST 11. | 12. leg w Cuff | 7. Rest 13. | 14. leg w Cuff | 9. OBST 15. |
|---|---|---|---|---|---|---|
| 16.1 | 17.96.7 | 18.97.5 | 19.377 | 20.377 | 21.445 | 22.389 |
| 23.2 | 24.98.1 | 25.98.5 | 26.351 | 27.334 | 28.393 | 29.339 |
| 30.3 | 31.96.5 | 32.95.5 | 33.378 | 34.387 | 35.418 | 36.419 |
| 37.4 | 38.95.9 | 39.95.2 | 40.335 | 41.322 | 42.363 | 43.331 |
| 44.5 | 45.95.3 | 46.94.2 | 47.383 | 48.388 | 49.438 | 50.393 |
| 51.6 | 52.95.5 | 53.95.5 | 54.394 | 55.387 | 56.449 | 57.400 |
| 58.8 | 59.96.9 | 60.97.0 | 61.337 | 62.339 | 63.383 | 64.347 |
| 65.9 | 66.97.4 | 67.98.3 | 68.364 | 69.369 | 70.398 | 71.368 |
| 72.10 | 73.100.0 | 74.100.0 | 75.368 | 76.376 | 77.401 | 78.364 |

TABLE A-continued

Results of the experiment are summarized in Table A:

| | 2. SATURATION | | 3. IPG | | | |
| | | | 6. Rest | | 8. OBST | |
| 1. | 4. Rest 10. | 5. OBST 11. | 12. leg w Cuff | 7. Rest 13. | 14. leg w Cuff | 9. OBST 15. |
|---|---|---|---|---|---|---|
| 79.11 | 80.98.4 | 81.100.0 | 82.360 | 83.371 | 84.420 | 85.374 |
| 86.12 | 87.97.0 | 88.100.0 | 89.372 | 90.375 | 91.396 | 92.345 |
| 93.13 | 94.96.3 | 95.97.3 | 96.431 | 97.414 | 98.504 | 99.418 |
| 100.14 | 101.97.0 | 102.97.8 | 103.383 | 104.379 | 105.423 | 106.379 |
| 107.Average | 108.97.0 | 109.97.5 | 110.371.8 | 111.370.6 | 112.417.8 | 113.374.3 |

The result in oxygen saturation remains at an average. The impedance wave significantly lengthens when there is an obstruction in a cuffed leg when compared with the non-cuffed leg, which did not have an obstruction.

The following novel quantifiable changes may be achieved through the system and method disclosed herein: delay in the peak perfusion wave arrival, in the presence of arterial obstruction in any extremity, relative to the ECG or the other extremities, and not just in the prolongation of the crest time; symmetrical delay in the peak perfusion filling wave to both legs, in the presence of arterial obstruction in abdominal aorta, relative to the ECG or the hands; significant changes in the shape of the perfusion wave, with slowing of the downslope; significant changes in the power spectrum of the perfusion wave, with attenuation of the higher frequencies, due to the huge changes in the cutoff frequency of the arterial system; ability to differentiate between the respiratory and cardiac modulations of the perfusion waves—the cardiac wave will usually appear above 1 Hz, and the respiratory modulation will appear at fifth of the heart rate (around 0.2 Hz); the ability to differentiate between the cardiac and respiratory component assists in classification of arterial versus venous lesions—partial venous occlusion will attenuate the respiratory component of the monitored perfusion waves; monitoring the coherence of the waves between the extremities, each one against the contralateral of the three others, increases the sensitivity; monitoring these indices over time (e.g. time delays, downslope rates, high frequency band of the arterial contents, cardiac versus breath bands and coherence between extremities) provides sensitive indices for early detection of progressive arterial or venous lesion; the above listed quantifiable indices are intended to be illustrative and not exclusive.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

In the description and claims of the application, each of the words "comprise" "include" and "have", and forms thereof, are not necessarily limited to members in a list with which the words may be associated. In addition, when there are inconsistencies between this application and any document incorporated by reference, it is hereby intended that the present application controls.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire. Rather, the computer readable storage medium is a non-transient (i.e., not-volatile) medium.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method for assessing obstruction in a blood vessel comprising:
    measuring a delay in wave propagation of a blood perfusion wave, which is associated with flow of blood through a blood vessel, and correlating said delay to an amount of occlusion in the blood vessel, wherein an increase in said delay is correlated as an increase in the amount of occlusion;
    wherein said delay is a peak perfusion delay that includes: (a) an interval from an R wave to a perfusion onset, also referred to as pulse-transit time; (b) a first phase of the perfusion wave and (c) a second phase of the perfusion wave, said second phase being faster than said first phase, up to a peak of the perfusion wave;
    identifying respiratory and cardiac components and modulations of said perfusion wave; and
    non-invasively detecting a presence of partial arterial occlusion in the blood vessel by correlating said partial arterial occlusion to an attenuation of the cardiac component of the perfusion wave, and graphically or numerically displaying a prolongation of said first phase of the perfusion wave, which is slower than said second phase, to graphically or numerically display existence of peripheral artery disease or arterial lesion.

2. The method according to claim 1, wherein said delay in wave propagation is associated with a change in a shape of said perfusion wave.

3. The method according to claim 1, wherein said delay in wave propagation is associated with a change in a power spectrum of said perfusion wave.

4. The method according to claim 1, further comprising measuring said delay in wave propagation in left and right limbs and comparing the delay in each of the limbs.

5. The method according to claim 1, wherein measuring said delay is done by measuring coherence between different limbs or sites, or between different acquisitions in time.

6. The method according to claim 1, wherein the correlating is done by wavelet coherence analysis, by continuous wavelet transform, or by analysis of a time-frequency domain associated with said delay.

7. The method according to claim 1, wherein differentiating between said respiratory and said cardiac components is done by quantifying changes in a spectrum between different limbs or sites or between different acquisitions in time.

8. A method for assessing obstruction in a blood vessel comprising:
    measuring a wave propagation of a blood perfusion wave, which is associated with flow of blood through a blood vessel;
    wherein said delay is a peak perfusion delay that includes: (a) an interval from an R wave to a perfusion onset, also referred to as pulse-transit time; (b) a first phase of the perfusion wave and (c) a second phase of the perfusion wave, said second phase being faster than said first phase, up to a peak of the perfusion wave;
    identifying respiratory and cardiac components and modulations of said perfusion wave; and
    non-invasively detecting a presence of partial arterial occlusion in the blood vessel by correlating said partial arterial occlusion to an attenuation of the cardiac component of the perfusion wave, and graphically or numerically displaying a prolongation of said first phase of the perfusion wave, which is slower than said second phase, to graphically or numerically display existence of peripheral artery disease or arterial lesion.

9. The method according to claim 8, wherein differentiating between said respiratory and said cardiac components is done by quantifying changes in a spectrum between different limbs or sites or between different acquisitions in time.

10. A system for assessing obstruction in a blood vessel comprising:
    a sensor configured to measure a delay in wave propagation of a blood perfusion wave, which is associated with flow of blood through a blood vessel, wherein said delay is a peak perfusion delay that includes: (a) an interval from an R wave to a perfusion onset, also referred to as pulse-transit time; (b) a first phase of the perfusion wave and (c) a second phase of the perfusion wave, said second phase being faster than said first phase, up to a peak of the perfusion wave; and
    a processor configured to correlate said delay to an amount of occlusion in the blood vessel, wherein an increase in said delay is correlated as an increase in the amount of occlusion;
    wherein said processor is configured to identify respiratory and cardiac components and modulations of said perfusion wave; and
    wherein said processor is configured to non-invasively detect a presence of partial arterial occlusion in the blood vessel by correlating said partial arterial occlusion to an attenuation of the cardiac component of the perfusion wave, and graphically or numerically displaying a prolongation of said first phase of the perfusion wave, which is slower than said second phase, on a graphic or numeric display to graphically or numerically display existence of peripheral artery disease or arterial lesion.

11. The system according to claim 10, wherein said sensor comprises an electrocardiogram (ECG) sensor.

12. The system according to claim 10, wherein said sensor comprises a photo-plethysmography (PPG) sensor.

13. The system according to claim 10, wherein said sensor comprises an impedance plethysmography (IPG) sensor.

14. The system according to claim 10, wherein said sensor comprises a tonometry sensor.

15. The system according to claim 10, wherein said sensor comprises an accelerometer.

* * * * *